(12) United States Patent
Genet et al.

(10) Patent No.: US 6,461,389 B1
(45) Date of Patent: *Oct. 8, 2002

(54) CATIONIC COUPLING AGENTS, THEIR USE FOR OXIDATION DYEING OF KERATINOUS FIBERS, DYEING COMPOSITIONS AND DYEING METHODS

(75) Inventors: Alain Genet, Aulnay-sous-Bois; Alain Lagrange, Coupvray, both of (FR)

(73) Assignee: L'Oreal S.A., Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 09/646,454

(22) PCT Filed: Mar. 15, 1999

(86) PCT No.: PCT/FR99/00575

§ 371 (c)(1),
(2), (4) Date: Nov. 13, 2000

(87) PCT Pub. No.: WO99/48874

PCT Pub. Date: Sep. 30, 1999

(30) Foreign Application Priority Data

Mar. 20, 1998 (FR) .......................................... 98 03456

(51) Int. Cl.⁷ ................................................. A61K 7/13
(52) U.S. Cl. ...................... 8/405; 8/407; 8/408; 8/410; 8/416; 546/184; 448/400
(58) Field of Search ............................ 8/405, 407, 408, 8/410, 411, 416

(56) References Cited

U.S. PATENT DOCUMENTS

| | | | |
|---|---|---|---|
| 3,100,739 A | 8/1963 | Kaiser et al. | 167/88 |
| 3,442,895 A | 5/1969 | Bugaut et al. | 260/247 |
| 3,528,972 A | 9/1970 | Kalopissis et al. | 260/247.1 |
| 4,823,985 A | 4/1989 | Grollier et al. | 222/1 |
| 4,888,025 A | 12/1989 | Bugaut et al. | 8/405 |
| 5,690,696 A * | 11/1997 | Bone et al. | 8/411 |
| 5,976,195 A * | 11/1999 | de al Mettrie et al. | 8/411 |

FOREIGN PATENT DOCUMENTS

| | | |
|---|---|---|
| BE | 616 439 | 10/1962 |
| DE | 1 135 589 | 8/1962 |
| DE | 1 292 784 | 4/1969 |
| EP | 0 544 400 | 6/1993 |
| FR | 1 391 675 | 6/1965 |
| FR | 2 520 358 | 7/1983 |
| FR | 2 586 913 | 3/1987 |
| WO | WO 95/01772 | 1/1995 |

OTHER PUBLICATIONS

Kimura et al. "Structure–activity relationship of N–(2–(Dimethylamino)–6–(3–(5–methyl–4–phenyl–H–imidazol–1–yl)propoxy)phenyl)–N'–pentyllurea and analogues." J.med.Chem. 1993, 36, 1630–1640.*

L.K.J. Tong et al., "The Mechanism of Dye Formation in Color Photography. VII. Intermediate Bases in the Deamination of Quinonediimines", Journal of the American Chemical Society, vol. 82, No. 7, Apr. 5, 1960, pp. 1988–1996.

Co–pending Application No. 09/646,455 (Int'l. Appln. No. PCT/FR99/00574), Inventor(s): Alain Genet et al., Filed: Sep. 19, 2000.

* cited by examiner

Primary Examiner—Yogendra N. Gupta
Assistant Examiner—Eisa B Elhilo
(74) Attorney, Agent, or Firm—Finnegan, Henderson, Farabow, Garrett & Dunner, L.L.P.

(57) ABSTRACT

The invention concerns novel monobenzene coupling agents comprising at least a cationic group Z, Z being selected among the aliphatic chains containing at least a quaternized unsaturated cycle, their use for oxidation dyeing of keratinous fibres dyeing compositions containing them and dyeing methods using same.

44 Claims, No Drawings

CATIONIC COUPLING AGENTS, THEIR USE FOR OXIDATION DYEING OF KERATINOUS FIBERS, DYEING COMPOSITIONS AND DYEING METHODS

The invention relates to novel monobenzenic couplers comprising at least one cationic group Z, Z being chosen from aliphatic chains comprising at least one quaternized unsaturated ring, to the use thereof for the oxidation dyeing of keratin fibres, to dye compositions containing them, and to oxidation dyeing processes using them.

It is known practice to dye keratin fibres, and in particular human hair, with dye compositions containing oxidation dye precursors, in particular ortho-phenylenediamines or para-phenylenediamines, ortho-aminophenols or para-aminophenols and heterocyclic compounds such as diaminopyrazole derivatives, which are generally referred to as oxidation bases. The oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds.

The variety of molecules used as oxidation bases and couplers makes it possible to obtain a wide range of colours.

The so-called "permanent" coloration obtained by means of these oxidation dyes must moreover satisfy a certain number of requirements. Thus, it must have no toxicological drawbacks and it must allow shades of the desired strength to be obtained and have good resistance to external agents (light, bad weather, washing, permanent-waving, perspiration and friction).

The dyes must also allow white hairs to be covered, and, lastly, they must be as unselective as possible, i.e. they must allow the smallest possible differences in coloration to be produced over the entire length of the same keratin fibre, which may indeed be differently sensitized (i.e. damaged) between its tip and its root.

It has already been proposed, in particular in patent application FR-A-2 520 358,to use certain cationic derivatives of meta-phenylenediamines, i.e. more specifically, certain meta-phenylenediamines monosubstituted with a quaternized aliphatic chain, for the oxidation dyeing of keratin fibres in intense shades. However, the use of the meta-phenylenediamines described in that prior patent application does not make it possible to obtain a wide variety of colours and, furthermore, the colorations obtained are not always entirely satisfactory as regards their resistance with respect to the various attacking factors to which the hair may be subjected (the action of light, perspiration, shampooing, etc.).

The Applicant has now discovered, entirely surprisingly and unexpectedly, that certain novel monobenzenic compounds of formula (I) defined below comprising at least one cationic group Z, Z being chosen from aliphatic chains comprising at least one quaternized unsaturated ring, are not only suitable for use as couplers for oxidation dyeing, but also make it possible to obtain dye compositions which give intense colorations, in a very wide range of shades, and which have excellent properties of resistance to the various treatments to which the keratin fibres may be subjected. Finally, these compounds are found to be easy to synthesize.

These discoveries form the basis of the present invention.

A first subject of the invention is thus novel compositions of formula (I) below, and the addition salts thereof with an acid:

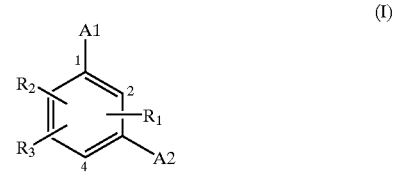

in which:

$R_1$, $R_2$ and $R_3$, which may be identical or different, represent a hydrogen atom; a halogen atom; a group Z; a group —CO—Z; a group —CO—OZ; a ($C_1$–$C_6$) alkylcarbonyl radical; an amino($C_1$–$C_6$)alkylcarbonyl radical; an N—Z-amino ($C_1$–$C_6$)alkylcarbonyl radical; an N—($C_1$–$C_6$)alkylamino($C_1$–$C_6$)alkylcarbonyl radical; an N,N-di($C_1$–$C_6$)alkylamino($C_1$–$C_6$) alkylcarbonyl radical; an amino($C_1$–$C_6$)alkylcarbonyl ($C_1$–$C_6$)alkyl radical; an N—Z-amino($C_1$–$C_6$) alkylcarbonyl($C_1$–$C_6$)alkyl radical; an N—($C_1$–$C_6$) alkylamino ($C_1$–$C_6$) alkylcarbonyl ($C_1$–$C_6$) alkyl radical; an N,N-di($C_1$–$C_6$)alkylamino($C_1$–$C_6$)alkylcarbonyl($C_1$–$C_6$)alkyl radical; a carboxyl radical; a ($C_1$–$C_6$)alkylcarboxyl radical; a $C_1$–$C_6$ alkylsulphonyl radical; an aminosulphonyl radical; an N—Z-aminosulphonyl radical; a $C_1$–$C_6$ N-alkylaminosulphonyl radical; an N,N-di ($C_1$–$C_6$) alkylaminosulphonyl radical; a $C_1$–$C_6$ aminosulphonylalkyl radical; a $C_1$–$C_6$ N—Z-aminosulphonylalkyl radical; an N—($C_1$–$C_6$) alkylaminosulphonyl($C_1$–$C_6$)alkyl radical; an N,N-di ($C_1$–$C_6$)alkylaminosulphonyl($C_1$–$C_6$)alkyl radical; a carbamyl radical; an N—($C_1$–$C_6$)alkylcarbamyl radical; an N,N-di($C_1$–$C_6$)alkylcarbamyl radical; a carbamyl($C_1$–$C_6$)alkyl radical; an N—($C_1$–$C_6$) alkylcarbamyl($C_1$–$C_6$)alkyl radical; an N,N-di($C_1$–$C_6$) alkylcarbamyl($C_1$–$C_6$)alkyl radical; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$) alkyl radical; a $C_1$–$C_6$ trifluoroalkyl radical; a cyano radical; a group $OR_6$ or $SR_6$; or an amino group protected with a ($C_1$–$C_6$)alkylcarbonyl, ($C_1$–$C_6$) alkylcarboxyl, trifluoro($C_1$–$C_6$)alkylcarbonyl, amino ($C_1$–$C_6$)alkylcarbonyl, N—Z-amino($C_1$–$C_6$) alkylcarbonyl, N—($C_1$–$C_6$)alkylamino($C_1$–$C_6$) alkylcarbonyl, N,N-di($C_1$–$C_6$)alkylamino($C_1$–$C_6$) alkylcarbonyl, ($C_1$–$C_6$) alkylcarboxyl, carbamyl, N—($C_1$–$C_6$) alkylcarbamyl, N,N-di($C_1$–$C_6$) alkylcarbamyl, $C_1$–$C_6$ alkylsulphonyl, aminosulphonyl, N—Z-aminosulphonyl, $C_1$–$C_6$ N-alkylaminosulphonyl, N,N-di($C_1$–$C_6$) alkylaminosulphonyl, thiocarbamyl or formyl radical, a group —CO—Z or a group —CO—OZ;

$R_6$ denotes a $C_1$–$C_6$ alkyl radical; a $C_1$–$C_6$ monohydroxyalkyl radical; a $C_2$–$C_6$ polyhydroxyalkyl radical; a group Z; a ($C_1$–$C_6$)alkoxy($C_1$–$C_6$)alkyl radical; an aryl radical; a benzyl radical; a carboxy($C_1$–$C_6$)alkyl radical; a ($C_1$–$C_6$)alkylcarboxy-($C_1$–$C_6$)alkyl radical; a cyano($C_1$–$C_6$)alkyl radical; a carbamyl($C_1$–$C_6$)alkyl radical; an N—($C_1$–$C_6$)alkylcarbamyl($C_1$–$C_6$)alkyl radical; an N,N-di($C_1$–$C_6$)alkylcarbamyl($C_1$–$C_6$)alkyl radical; a $C_1$–$C_6$ trifluoroalkyl radical; a $C_1$–$C_6$ aminosulphonylalkyl radical; a $C_1$–$C_6$ N—Z-aminosulphonylalkyl radical; an N—($C_1$–$C_6$)

alkylaminosulphonyl($C_1$–$C_6$)alkyl radical; an N,N-di($C_1$–$C_6$)alkylaminosulphonyl($C_1$–$C_6$)alkyl radical; a ($C_1$–$C_6$)alkylsulphinyl($C_1$–$C_6$)alkyl radical; a ($C_1$–$C_6$)alkylsulphonyl($C_1$–$C_6$)alkyl radical; a ($C_1$–$C_6$)alkylcarbonyl($C_1$–$C_6$)alkyl radical; a $C_1$–$C_6$ aminoalkyl radical; a $C_1$–$C_6$ aminoalkyl radical in which the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$)alkylcarbonyl, formyl, trifluoro-($C_1$–$C_6$)alkylcarbonyl, ($C_1$–$C_6$)alkylcarboxyl, carbamyl, N—($C_1$–$C_6$)alkylcarbamyl, N,N-di-($C_1$–$C_6$)alkylcarbamyl, thiocarbamyl and $C_1$–$C_6$ alkylsulphonyl radicals, and from the groups Z, —CO—Z and —CO—OZ;

A1 represents a group —$NR_4R_5$ or a hydroxyl radical;

A2 represents a group —$NR'_4R'_5$ or a hydroxyl radical;

$R_4$, $R'_4$, $R_5$ and $R'_5$, which may be identical or different, represent a hydrogen atom; a group Z; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; an aryl radical; a benzyl radical; a cyano($C_1$–$C_6$)alkyl radical; a carbamyl($C_1$–$C_6$)alkyl radical; an N—($C_1$–$C_6$)alkylcarbamyl($C_1$–$C_6$)alkyl radical; an N,N-di($C_1$–$C_6$)alkylcarbamyl($C_1$–$C_6$)alkyl radical; a thiocarbamyl($C_1$–$C_6$)alkyl radical; a $C_1$–$C_6$ trifluoroalkyl radical; a $C_1$–$C_6$ sulphoalkyl radical; a ($C_1$–$C_6$)alkylcarboxy($C_1$–$C_6$)alkyl radical; a ($C_1$–$C_6$)alkylsulphinyl($C_1$–$C_6$)alkyl radical; a $C_1$–$C_6$ aminosulphonylalkyl radical; a $C_1$–$C_6$ N—Z-aminosulphonylalkyl radical; an N—($C_1$–$C_6$)alkylaminosulphonyl($C_1$–$C_6$)alkyl radical; an N,N-di($C_1$–$C_6$)alkylaminosulphonyl($C_1$–$C_6$)alkyl radical; a ($C_1$–$C_6$)alkylcarbonyl($C_1$–$C_6$)alkyl radical; a $C_1$–$C_6$ aminoalkyl radical; a $C_1$–$C_6$ aminoalkyl radical in which the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$)alkylcarbonyl, carbamyl, N—($C_1$–$C_6$)alkylcarbamyl or N,N-di($C_1$–$C_6$)alkylcarbamyl, $C_1$–$C_6$ alkylsulphonyl, formyl, trifluoro($C_1$–$C_6$)alkylcarbonyl, ($C_1$–$C_6$)alkylcarboxyl and thiocarbamyl radicals, or with a group Z, —CO—Z or —CO—OZ; one and only one of the radicals $R_4$, $R'_4$, $R_5$ and $R'_5$ can also represent a ($C_1$–$C_6$)alkylcarboxyl radical; a ($C_1$–$C_6$)alkylcarbonyl radical; a formyl radical; a trifluoro($C_1$–$C_6$)alkylcarbonyl radical; an amino($C_1$–$C_6$)alkylcarbonyl radical; an N—Z-amino($C_1$–$C_6$)alkylcarbonyl radical; an N—($C_1$–$C_6$)alkylamino($C_1$–$C_6$)alkylcarbonyl radical; an N,N-di($C_1$–$C_6$)alkylamino($C_1$–$C_6$)alkylcarbonyl radical; a carbamyl radical; an N—($C_1$–$C_6$)alkylcarbamyl radical; an N,N-di($C_1$–$C_6$)alkylcarbamyl radical; a thiocarbamyl radical; an aminosulphonyl radical; an N—Z-aminosulphonyl radical; an N—($C_1$–$C_6$)alkylaminosulphonyl radical; an N,N-di($C_1$–$C_6$)alkylaminosulphonyl radical; a ($C_1$–$C_6$)alkylsulphonyl radical; a group —CO—Z or a group —CO—OZ;

Z is chosen from the unsaturated cationic groups of formulae (II) and (III) below, and the saturated cationic groups of formula (IV) below:

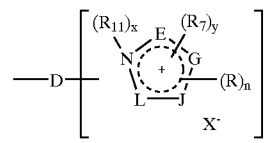

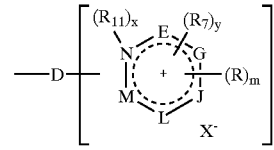

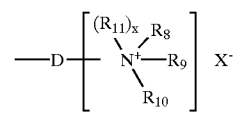

in which:

D is a linker arm which represents a linear or branched alkyl chain preferably containing from 1 to 14 carbon atoms, which may be interrupted by one or more hetero atoms such as oxygen, sulphur or nitrogen atoms, and which may be substituted with one or more hydroxyl or $C_1$–$C_6$ alkoxy radicals;

the ring members E, G, J, L and M, which may be identical or different, represent a carbon, oxygen, sulphur or nitrogen atom;

n is an integer between 0 and 4 inclusive;

m is an integer between 0 and 5 inclusive;

the radicals R, which may be identical or different, represent a group Z, a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano($C_1$–$C_6$)alkyl radical, a $C_1$–$C_6$ alkoxy radical, a tri($C_1$–$C_6$)alkylsilane($C_1$–$C_6$)alkyl radical, an amido radical, an aldehydo radical, a carboxyl radical, a ($C_1$–$C_6$)alkylcarbonyl radical, a thio radical, a $C_1$–$C_6$ thioalkyl radical, a $C_1$–$C_6$ alkylthio radical, an amino radical, an amino radical protected with a ($C_1$–$C_6$)alkylcarbonyl, carbamyl or $C_1$–$C_6$ alkylsulphonyl radical; a group NHR" or NR"R"' in which R" and R"', which may be identical or different, represent a $C_1$–$C_6$ alkyl radical, a $C_1$–$C_6$ monohydroxyalkyl radical or a $C_2$–$C_6$ polyhydroxyalkyl radical;

when n is greater than or equal to 2, two of the adjacent radicals R can also form together an unsaturated 5- or 6-membered carbon-based ring or a ring containing one or more hetero atoms;

$R_7$ represents a $C_1$–$C_6$ alkyl radical, a $C_1$–$C_6$ monohydroxyalkyl radical, a $C_2$–$C_6$ polyhydroxyalkyl radical, a cyano($C_1$–$C_6$)alkyl radical, a tri($C_1$–$C_6$)alkylsilane($C_1$–$C_6$)alkyl radical, a ($C_1$–$C_6$)alkoxy($C_1$–$C_6$)alkyl radical, a carbamyl($C_1$–$C_6$)alkyl radical, a ($C_1$–$C_6$)alkylcarboxy($C_1$–$C_6$)alkyl radical, a benzyl radical or a group Z of formula (II), (III) or (IV) as defined above;

$R_8$, $R_9$ and $R_{10}$, which may be identical or different, represent a $C_1$–$C_6$ alkyl radical, a $C_1$–$C_6$ monohydroxyalkyl radical, a $C_2$–$C_6$ polyhydroxyalkyl radical, a ($C_1$–$C_6$)alkoxy($C_1$–$C_6$)alkyl radical, a cyano($C_1$–$C_6$)alkyl radical, an aryl radical, a benzyl radical, an amido($C_1$–$C_6$)alkyl radical, a tri($C_1$–$C_6$)alkylsilane($C_1$–$C_6$)alkyl radical or a $C_1$–$C_6$ aminoalkyl radical in which the amine is protected with a $(C_1-C_6)$alkylcarbonyl, carbamyl or $C_1-C_6$ alkylsulphonyl radical; two of the radicals $R_7$, $R_8$ and $R_9$ can also form, together with the nitrogen atom to which they are attached, a 5- or 6-membered saturated carbon-based ring or a ring containing one or more hetero atoms, such as, for example, a pyrrolidine ring, a piperidine ring, a piperazine ring or a morpholine ring, it being possible for the said ring to be unsubstituted or substituted with a halogen atom, a hydroxyl radical, a $C_1-C_6$ alkyl radical, a $C_1-C_6$ monohydroxyalkyl radical, a $C_2-C_6$ polyhydroxyalkyl radical, a nitro radical, a cyano radical, a cyano$(C_1-C_6)$alkyl radical, a $C_1-C_6$ alkoxy radical, a tri$(C_1-C_6)$alkylsilane$(C_1-C_6)$alkyl radical, an amido radical, an aldehydo radical, a carboxyl radical, a keto$(C_1-C_6)$alkyl radical, a thio radical, a $C_1-C_6$ thioalkyl radical, a $C_1-C_6$ alkylthio radical, an amino radical or an amino radical protected with a $(C_1-C_6)$alkylcarbonyl, carbamyl or $C_1-C_6$ alkylsulphonyl radical;

one of the radicals $R_8$, $R_9$ and $R_{10}$ can also represent a radical D' of a second group Z, D' having the same meanings as those indicated above for D;

$R_{11}$ represents a $C_1-C_6$ alkyl radical; a $C_1-C_6$ monohydroxyalkyl radical; a $C_2-C_6$ polyhydroxyalkyl radical; an aryl radical; a benzyl radical; a $C_1-C_6$ aminoalkyl radical, a $C_1-C_6$ aminoalkyl radical in which the amine is protected with a $(C_1-C_6)$ alkylcarbonyl, carbamyl or $C_1-C_6$ alkylsulphonyl radical; a carboxy$(C_1-C_6)$alkyl radical; a cyano $(C_1-C_6)$alkyl radical; a carbamyl$(C_1-C_6)$alkyl radical; a $C_1-C_6$ trifluoroalkyl radical; a tri$(C_1-C_6)$ alkylsilane$(C_1-C_6)$alkyl radical; a sulphonamido $(C_1-C_6)$alkyl radical; a $(C_1-C_6)$alkylcarboxy $(C_1-C_6)$alkyl radical; a $(C_1-C_6)$alkylsulphinyl $(C_1-C_6)$alkyl radical; a $(C_1-C_6)$alkylsulphonyl $(C_1-C_6)$alkyl radical; a $(C_1-C_6)$alkylketo$(C_1-C_6)$ alkyl radical; an N—$(C_1-C_6)$alkylcarbamyl$(C_1-C_6)$ alkyl radical; an N—$(C_1-C_6)$alkylsulphonamido $(C_1-C_6)$alkyl radical;

x and y are integers equal to 0 or 1; with the following conditions:

in the unsaturated cationic groups of formula (II):
when x=0, the linker arm D is attached to the nitrogen atom,
when x=1, the linker arm D is attached to one of the ring members E, G, J or L,
y cannot take the value 1 except: 1) when the ring members E, G, J and L simultaneously represent a carbon atom, and when the radical $R_7$ is borne by the nitrogen atom of the unsaturated ring; or alternatively 2) when at least one of the ring members E, G, J and L represents a nitrogen atom to which the radical $R_7$ is attached;

in the unsaturated cationic groups of formula (III):
when x=0, the linker arm D is attached to the nitrogen atom,
when x=1, the linker arm D is attached to one of the ring members E, G, J, L or M,
y cannot take the value 1 except when at least one of the ring members E, G, J, L and M represents a divalent atom, and when the radical $R_7$ is borne by the nitrogen atom of the unsaturated ring;

in the cationic groups of formula (IV):
when x=0, then the linker arm is attached to the nitrogen atom bearing the radicals $R_8$ to $R_{10}$, when x=1, then two of the radicals $R_8$ to $R_{10}$ form, together with the nitrogen atom to which they are attached, a saturated 5- or 6-membered ring as defined above, and the linker arm B is borne by a carbon atom of the said saturated ring;

$X^-$ represents a monovalent or divalent anion and is preferably chosen from a halogen atom such as chlorine, bromine, fluorine or iodine, a hydroxide, a hydrogen sulphate and a $C_1-C_6$ alkyl sulphate such as, for example, a methyl sulphate or an ethyl sulphate;

it being understood that the number of unsaturated cationic groups Z of formula (II) or (III) is at least equal to 1, and with the exclusion of the compound of the following formula:

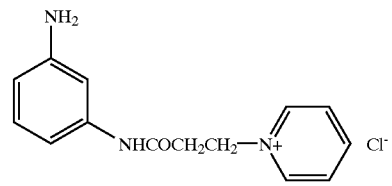

which is a compound which is known as an intermediate for the manufacture of azo dyes: see in particular patent application DE 1 135 589.

As mentioned above, the colorations obtained with the oxidation dye composition in accordance with the invention are intense and make it possible to obtain a very wide range of colours. Moreover, they have excellent properties of resistance with respect to the action of various external agents (light, bad weather, washing, permanent-waving, perspiration, rubbing). These properties are particularly noteworthy in particular as regards the resistance of the colorations obtained with respect to the action of light.

In formula (I) above, the alkyl and alkoxy radicals may be linear or branched.

Among the rings of the unsaturated groups Z of formula (II) above, mention may be made in particular, by way of example, of pyrrole, imidazole, pyrazole, oxazole, thiazole, triazole, pyrazolopyrimidinium, pyrazolopyridinium, benzoimidazolinium, benzoxazolinium, benzothiazolinium, indolinium, indolidinium, isoindolinium, indazolinium, benzotriazolinium, benzoimidazolidinium and benzopyrimidinium rings.

Among the rings of the unsaturated groups Z of formula (III) above, mention may be made in particular, by way of example, of pyridine, pyrimidine, pyrazine, oxazine, triazine, pyrazolopyrimidinium, pyrazolopyridinium, quinolinium and tetrahydroquinolinium rings. Among the compounds of formula (I) above, mention may be made in particular of:

1-[3-(2,4-diaminophenoxy)propyl]-3-methyl-3H-imidazol-1-ium chloride;

1-[(3-hydroxy-4-methylphenylcarbamoyl)methyl]-3-methyl-3H-imidazol-1-ium chloride;

3-ethyl-1-[(3-hydroxyphenylcarbamoyl)methyl]-3H-imidazol-1-ium chloride;

1-[(3-hydroxy-2,4-dimethylphenylcarbamoyl)methyl]-3-methyl-3H-imidazol-1-ium chloride;

1-[(4-chloro-3-hydroxyphenylcarbamoyl)methyl]-3-methyl-3H-imidazol-1-ium chloride;

1-[(3-hydroxy-4-methoxyphenylcarbamoyl)methyl]-3-methyl-3H-imidazol-1-ium chloride;

1-[(3-hydroxy-4-methylphenylcarbamoyl)methyl]-2-methyl-2H-pyrazol-1-ium chloride;

1-[2-(3-hydroxy-4-methylphenylamino)ethyl]-3-methyl-3H-imidazol-1-ium bromide;

1-[2-(3-hydroxy-4-methylphenylcarbamoyloxy)ethyl]-2,3-dimethyl-3H-imidazol-1-ium chloride;

1-{[3-amino-4-(3-(3-methyl-3H-imidazol-1-ium)propoxy)phenylcarbamoyl]methyl}-3-methyl-3H-imidazol-1-ium dichloride;

3-(3-trimethylammonium-2-hydroxypropyl)-1-[(3-hydroxy-4-methylphenylcarbamoyl)methyl]-3H-imidazol-1-ium dichloride;

1-{[2-(2-(2,4-diaminophenoxy)ethylcarbamoyl]methyl}-3-methyl-3H-imidazol-1-ium chloride;

1-[(2,4-dihydroxyphenylcarbamoyl)methyl]-3-methyl-3H-imidazol-1-ium chloride;

N,N-bis[2-(3-methyl-3H-imidazol-1-ium)ethyl]benzene-1,3-diamine dichloride;

1-{3-[4-amino-2-(2-triethylammoniumacetylamino)phenoxy]propyl}-3-methyl-3H-imidazol-1-ium dichloride;

1-(3-{4-amino-2-[2-(3-methyl-3H-imidazol-1-ium)acetylamino]phenoxy}propyl)-1,4-dimethylpiperazin-1-ium dichloride;

1-[2-(2,4-dihydroxyphenyl)-2-oxoethyl]-3-methyl-3H-imidazol-1-ium chloride;

1-[2-(2,4-diaminophenyl)ethyl]-3-methyl-3H-imidazol-1-ium chloride;

and the addition salts thereof with an acid.

The compounds of formula (I) in accordance with the invention can readily be obtained, according to methods that are well known in the prior art, for example by reducing the corresponding cationic nitro compounds (cationic meta-nitroanilines or cationic meta-nitrophenols).

This reduction step (production of a primary aromatic amine), optionally followed by a salification, is generally, for the sake of convenience, the final step in the synthesis.

This reduction can be carried out earlier in the sequence of reactions leading to the preparation of compounds of formula (I), and according to well-known processes, in which case it is necessary to "protect" the primary amine created (for example by means of an acetylation, benzenesulphonation, etc. step) and then carry out the desired substitution(s) or modification(s) (including quarternization) and end by "deprotecting" (generally in acidic medium) the amine function.

Similarly, the phenolic function can be protected according to well-known processes, by means of a benzyl radical ("deprotection" by catalytic reduction) or by means of an acetyl or mesyl radical ("deprotection" in acidic medium).

When the synthesis is complete, the compounds of formula (I) in accordance with the invention can, if necessary, be recovered by methods that are well known in the prior art, such as crystallization or distillation.

Another subject of the invention is the use of the compounds of formula (I) in accordance with the invention as couplers for the oxidation dyeing of keratin fibres, and in particular of human keratin fibres such as the hair.

A subject of the invention is also a composition for the oxidation dyeing of keratin fibres, and in particular of human keratin fibres such as the hair, characterized in that it comprises, as coupler, in a medium which is suitable for dyeing, at least one compound of formula (I) in accordance with the invention.

The compound(s) of formula (I) in accordance with the invention and/or the addition salt(s) thereof with an acid preferably represent(s) from 0.0005 to 12% by weight approximately relative to the total weight of the dye composition, and even more preferably from 0.005 to 6% by weight approximately relative to this weight.

According to one preferred embodiment of the invention, the dye composition also contains one or more oxidation bases which can be chosen from the oxidation bases conventionally used in oxidation dyeing and among which mention may be made in particular of para-phenylenediamines, bis(phenyl)alkylenediamines, para-aminophenols, ortho-aminophenols and heterocyclic bases.

Among the para-phenylenediamines which can be mentioned more particularly, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N—(β-hydroxypropyl)-para-phenylenediamine, 2-hydroxymethyl-para-phenylenediamine, N,N-dimethyl-3-methyl-para-phenylenediamine, N-ethyl-N—(β-hydroxyethyl)-para-phenylenediamine, N—(β,γ-dihydroxypropyl)-para-phenylenediamine, N—(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N—(β-methoxyethyl)-para-phenylenediamine, and the addition salts thereof with an acid.

Among the para-phenylenediamines mentioned above, the ones most particularly preferred are para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid.

Among the bis(phenyl)alkylenediamines which can be mentioned more particularly, for example, are N,N'-bis(β-hydroxyethyl)-N,N'-bis (4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the addition salts thereof with an acid.

Among the para-aminophenols which can be mentioned more particularly, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols which can be mentioned more particularly, for example, are 2-aminophenol, 2-amino-5-methylphenol, 2-amino-6-methylphenol and 5-acetamido-2-aminophenol, and the addition salts thereof with an acid.

Among the heterocyclic bases which can be mentioned more particularly, for example, are pyridine derivatives, pyrimidine derivatives and pyrazole derivatives.

When they are used, these oxidation base(s) preferably represent(s) from 0.0005 to 12% by weight approximately relative to the total weight of the dye composition, and even more preferably from 0.005 to 6% by weight approximately relative to this weight.

In addition to the compound(s) of formula (I) above, the dye composition in accordance with the invention can also include one or more additional couplers which can be chosen from the couplers used conventionally in oxidation dyeing and among which mention may be made in particular of meta-phenylenediamines, meta-aminophenols, meta-diphenols and heterocyclic couplers such as, for example, indole derivatives, indolene derivatives, pyridine derivatives and pyrazolones, and the addition salts thereof with an acid.

These couplers are chosen more particularly from 2-methyl-5-aminophenol, 5-N—(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, a-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one, and the addition salts thereof with an acid.

When they are present, these couplers preferably represent from 0.0001 to 10% by weight approximately relative to the total weight of the dye composition and even more preferably from 0.005 to 5% by weight approximately relative to this weight.

In general, the addition salts with an acid which can be used in the context of the invention (compounds, of formula (I), additional oxidation bases and couplers) are chosen in particular from the hydrochlorides, hydrobromides, sulphates, citrates, succinates, tartrates, lactates and acetates.

The medium which is suitable for dyeing (or support) generally consists of water or of a mixture of water and at least one organic solvent to dissolve the compounds which would not be sufficiently soluble in water. As organic solvent, mention may be made, for example, of $C_1$–$C_4$ lower alkanols;, such as ethanol and isopropanol; glycerol; glycols and glycol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, similar products and mixtures thereof.

The solvents can be present in proportions preferably of between 1 and 40% by weight approximately relative to the total weight of the dye composition, and even more preferably between 5 and 30% by weight approximately.

The pH of the dye composition in accordance with the invention is generally between 3 and 12 approximately, and preferably between 5 and 11 approximately. It can be adjusted to the desired value using acidifying or basifying agents commonly used to dye keratin fibres.

Among the acidifying agents which may be mentioned, for example, are inorganic or organic acids such as hydrochloric acid, orthophosphoric acid, sulphuric acid, carboxylic acids such as acetic acid, tartaric acid, citric acid and lactic acid, and sulphonic acids.

Among the basifying agents which can be mentioned, for example, are aqueous ammonia, alkaline carbonates, alkanolamines such as mono-, di- and triethanolamine and derivatives thereof, sodium hydroxide, potassium hydroxide and the compounds of formula (V) below:

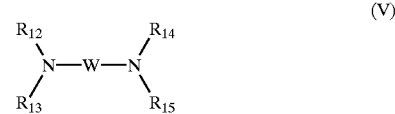

in which W is a propylene residue optionally substituted with a hydroxyl group or a $C_1$–$C_6$ alkyl radical; $R_{12}$, $R_{13}$, $R_{14}$ and $R_{15}$, which may be identical or different, represent a hydrogen atom, a $C_1$–$C_6$ alkyl radical or a $C_1$–$C_6$ hydroxyalkyl radical.

The oxidation dye compositions in accordance with the invention can also include at least one direct dye, in particular in order to modify the shades or to enrich them with glints.

The dye composition in accordance with the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, packaging agents such as, for example, silicones, which may or may not be volatile or modified, film-forming agents, ceramides, preserving agents and opacifiers.

Needless to say, a person skilled in the art will take care to select this or these optional additional compound(s) such that the advantageous properties intrinsically associated with the oxidation dye composition in accordance with the invention are not, or are not substantially, adversely affected by the addition(s) envisaged.

The dye composition according to the invention can be in various forms, such as in the form of liquids, creams or gels or in any other form which is suitable for dyeing keratin fibres, and in particular human hair.

The invention also relates to a process for the oxidation dyeing of keratin fibres, and in particular of human keratin fibres such as the hair, using the dye composition as defined above.

According to this process, at least one dye composition as defined above is applied to the fibres, the colour being developed at acidic, neutral or alkaline pH using an oxidizing agent which is added, just at the time of use, to the dye composition, or which is present in an oxidizing composition that is applied simultaneously or sequentially.

According to a preferred embodiment of the dyeing process of the invention, the dye composition described above is preferably mixed, at the time of use, with an oxidizing composition containing, in a medium which is suitable for dyeing, at least one oxidizing agent present in an amount which is sufficient to develop a coloration. The mixture obtained is then applied to the keratin fibres and is left in place for 3 to 50 minutes approximately, preferably 5 to 30 minutes approximately, after which the fibres are rinsed, washed with shampoo, rinsed again and dried.

The oxidizing agent can be chosen from the oxidizing agents conventionally used for the oxidation dyeing of keratin fibres, and among which mention may be made of hydrogen peroxide, urea peroxide, alkali metal bromates, persalts such as perborates and persulphates, and enzymes such as peroxidases and 2-electron oxidoreductases. Hydrogen peroxide is particularly preferred.

The pH of the oxidizing composition containing the oxidizing agent as defined above is such that, after mixing with the dye composition, the pH of the resultant composition applied to the keratin fibres preferably varies between 3 and 12 approximately, and even more preferably between 5 and 11. It is adjusted to the desired value using acidifying or basifying agents commonly used to dye keratin fibres and as defined above.

The oxidizing composition as defined above can also contain various adjuvants conventionally used in compositions for dyeing the hair and as defined above.

The composition which is finally applied to the keratin fibres can be in various forms, such as in the form of liquids, creams, gels or any other form which is suitable for dyeing keratin fibres, and in particular human hair.

Another subject of the invention is a multi-compartment dyeing device or "kit" or any other multi-compartment packaging system, a first compartment of which contains the dye composition as defined above and a second compartment of which contains the oxidizing composition as defined above. These devices can be equipped with a means for delivering the desired mixture onto the hair, such as the devices described in patent FR 2 586 913 in the name of the Applicant.

The examples which follow are intended to illustrate the invention without thereby limiting its scope.

PREPARATION EXAMPLES

Preparation Example 1

Preparation of 1-[3-(2,4-Diaminophenoxy)propyl]-3-methyl-3H-imidazol-1-ium Chloride Dihydrochloride

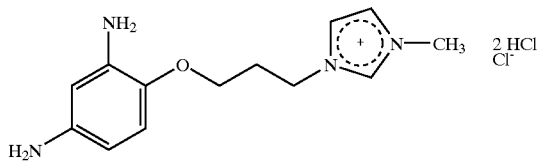

a) Synthesis of N-[2-(3-Chloropropoxy)-5-nitrophenyl] acetamide

A mixture of 186.5 g (0.94 mol) of N—(2-hydroxy-5-nitrophenyl)acetamide and 142.7 g (1.03 mol) of potassium carbonate in 570 ml of dimethylformamide was heated to 30–35° C. with stirring; 444.0 g (2.82 mol) of 1-bromo-3-chloropropane were then added and heating was continued at 40° C. for 7 hours (orange-coloured suspension).

The mixture was poured into 3 liters of ice-cold water and the crystalline precipitate was spin-filtered, reslurried in water and then in isopropyl alcohol and dried under vacuum at 40° C. over phosphorus pentoxide.

After purification by recrystallization from refluxing isobutanol, 203.0 g of beige crystals were obtained, which melted at 134° C. (Kofler) and the elemental analysis of which, calculated for $C_{11}H_{13}N_2O_4Cl$, was:

| % | C | H | N | O | Cl |
|---|---|---|---|---|---|
| Calculated | 48.45 | 4.81 | 10.27 | 23.47 | 13.00 |
| Found | 48.58 | 4.79 | 10.25 | 23.50 | 13.20 | b) Synthesis of 1-[3-(2-Acetylamino-4-nitrophenoxy)propyl]-3-methyl-3H-imidazol-1-ium Chloride 40.0 g (0.146 mol) of N-[2-(3-chloropropoxy)-5-nitrophenyl]acetamide obtained above in the preceding step and 14.3 g (0.175 mol) of methyl-1H-imidazole were suspended in 150 ml of 2-methyl-1-pentanol.

The mixture was refluxed for 12 hours with stirring and cooled, and the crystalline precipitate was spin-filtered and reslurried twice in absolute ethanol.

After recrystallization from refluxing 96° ethanol, pale yellow crystals (29.8 g) of 1-[3-(2 -acetylamino-4-nitrophenoxy)propyl]-3-methyl-3H-imidazol-1-ium were obtained, melting at 190° C. (Kofler), the elemental analysis of which, calculated for $C_{15}H_{19}N_4O_4Cl$, was:

| % | C | H | N | O | Cl |
|---|---|---|---|---|---|
| Calculated | 50.78 | 5.40 | 15.79 | 18.04 | 9.99 |
| Found | 50.36 | 5.36 | 15.69 | 17.99 | 10.03 | c) Synthesis of 1-[3-(2-Acetylamino-4-aminophenoxy)propyl]-3-methyl-3H-imidazol-1-ium Chloride Monohydrate 19.0 g (0.0535 mol) of 1-[3-(2-acetylamino-4-nitrophenoxy)propyl]-3-methyl-3H-imidazol-1-ium obtained above in the preceding step, 8 g of 5% palladium-on-charcoal (containing 50% water), 150 ml of 96° ethanol and 150 mol of water were placed in a hydrogenator.

The reduction took place over ½ hour under a hydrogen pressure of about 8 bar and at a temperature which was raised gradually to 75° C. After filtering off the catalyst under nitrogen, the filtrate was evaporated to dryness under reduced pressure.

The crystalline compound obtained was purified by recrystallization from refluxing ethanol.

13.2 g of off-white crystals were obtained which melted at 136° C. (Kofler), and the elemental analysis of which, calculated for $C_{15}H_{21}N_4O_2Cl \cdot H_2O$ was:

| % | C | H | N | O | Cl |
|---|---|---|---|---|---|
| Calculated | 52.55 | 6.76 | 16.34 | 14.00 | 10.34 |
| Found | 52.32 | 6.78 | 16.34 | 14.39 | 10.14 | d) Deacetylation

A solution of 13.1 g (0.0382 mol) of 1-[3-(2-acetylamino-4-aminophenoxy)propyl]-3-methyl-3H-imidazol-1-ium chloride monohydrate, obtained above in the preceding step, in 26 ml of aqueous 36% hydrochloric acid was heated for 1 hour on a boiling water bath.

The mixture was cooled in a bath of ice, diluted with 50 ml of absolute ethanol, spin-filtered, washed with absolute ethanol and dried at 45° C. under vacuum and over potassium hydroxide.

12.7 g of white crystals of 1-[3-(2,4-diaminophenoxy)propyl]-3-methyl-3H-imidazol-1-ium chloride, dihydrochloride were obtained, melting with decomposition at above 260° C. (Kofler), and the elemental analysis of which, calculated for $C_{13}H_{21}N_4OCl_3$ was:

| % | C | H | N | O | Cl |
|---|---|---|---|---|----|
| Calculated | 43.90 | 5.95 | 15.75 | 4.50 | 29.90 |
| Found | 43.97 | 5.99 | 15.67 | 4.70 | 29.78 |

Preparation Example 2

Preparation of 1-[(3-Hydroxy-4-methylphenylcarbamoyl)methyl]-3-methyl-3H-imidazol-1-ium Chloride

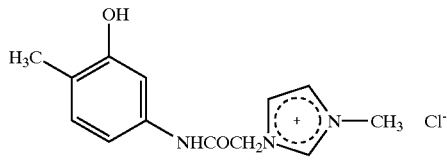

36.6 g (0.183 mol) of 2-chloro-N—(3-hydroxy-4-methylphenyl)acetamide and 29.2 ml (0.366 mol) of 1-methyl-1H-imidazole in 180 ml of toluene were refluxed for one and a half hours.

The crystalline precipitate formed was spin-filtered and reslurried in toluene.

After recrystallization from refluxing 95° ethanol, 32.1 g of white crystals of 1-[(3-hydroxy-4-methylphenylcarbamoyl)methyl]-3-methyl-3H-imidazol-1-ium were obtained, which melted at 236° C. (Kofler) and the elemental analysis of which, calculated for $C_{13}H_{16}N_3O_2Cl$, was:

| % | C | H | N | O | Cl |
|---|---|---|---|---|----|
| Calculated | 55.42 | 5.72 | 14.91 | 11.36 | 12.58 |
| Found | 55.20 | 5.71 | 14.81 | 11.62 | 12.56 |

APPLICATION EXAMPLES

Dyeing Examples 1 and 2

The dye compositions below were prepared (contents in grams):

| EXAMPLE | 1 | 2 |
|---|---|---|
| 1-[3-(2,4-Diaminophenoxy)propyl]-3-methyl-3H-imidazol-1-ium chloride dihydrochloride (compound of formula (I)) | 1.066 | 1.066 |
| para-Phenylenediamine (oxidation base) | 0.324 | — |
| para-Aminophenol (oxidation base) | — | 0.327 |
| Common dye support No. 1 | (*) | (*) |
| Demineralized water qs | 100 g | 100 g |

(*) Common dye support No. 1:
| 96° ethanol | 18 g |
| Sodium metabisulphite as an aqueous 35% solution | 0.68 g |

| Pentasodium salt of diethylenetriaminepentaacetic acid | 1.1 g |
| Aqueous ammonia containing 20% $NH_3$ | 10.0 g |
| Demineralized water qs | 100 g |

At the time of use, each of the above dye compositions was mixed weight for weight with a 20-volumes hydrogen peroxide solution (6% by weight) of pH 3.

The mixture obtained was applied to locks of natural grey hair containing 90% white hairs for 30 minutes. The locks were then rinsed, washed with a standard shampoo, rinsed again and then dried.

The shades obtained are given in the table below:

| EXAMPLE | Dyeing pH | Shade obtained |
|---|---|---|
| 1 | 10 ± 0.2 | Muted-blue light chestnut |
| 2 | 10 ± 0.2 | Ash-red chestnut |

Dyeing Examples 3 to 5

The dye compositions below were prepared (contents in grams):

| EXAMPLE | 3 | 4 | 5 |
|---|---|---|---|
| 1-[(3-Hydroxy-4-methylphenyl-carbamoyl)methyl]-3-methyl-3H-imidazol-1-ium chloride (compound of formula (I)) | 0.845 | 0.845 | 0.845 |
| para-Phenylenediamine dihydrochloride (oxidation base) | 0.543 | — | — |
| para-Tolylenediamine dihydrochloride (oxidation base) | — | 0.585 | — |
| 3,7-Diaminopyrazolopyrimidine dihydrochloride (oxidation base) | — | — | 0.666 |
| Common dye support No. 2 | () | () | (**) |
| Demineralized water qs | 100 g | 100 g | 100 g |

(**) Common dye support No. 2:
| Oleyl alcohol polyglycerolated with 2 mol of glycerol | 4.0 g |
| Oleyl alcohol polyglycerolated with 4 mol of glycerol containing 78% active material (A.M.) | 5.69 g A.M. |
| Oleic acid | 3.0 g |
| Oleyl amine containing 2 mol of ethylene oxide, sold under the trade name ETHOMEEN O12 ® by the company AKZO | 7.0 g |
| Diethylaminopropyl laurylamino succinamate, sodium salt, containing 55% A.M. | 3.0 g A.M. |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite as an aqueous solution containing 35% A.M. | 0.455 g A.M. |
| Ammonium acetate | 0.8 g |
| Antioxidant, sequestering agent | q.s. |
| Fragrance, preserving agent | q.s. |
| Aqueous ammonia containing 20% of $NH_3$ | 10.0 g |

At the time of use, each of the above dye compositions was mixed weight for weight with a 20-volumes hydrogen peroxide solution (6% by weight) of pH 3.

The mixture obtained was applied to locks of natural or permanent-waved grey hair containing 90% of white hairs, for 30 minutes. The locks were then rinsed, washed with a standard shampoo, rinsed again and then dried.

The shades obtained are given in the table below:

| EXAMPLE | Dyeing pH | Shade obtained on natural hair | Shade obtained on permanent-waved hair |
|---------|-----------|-------------------------------|----------------------------------------|
| 3 | 9.7 ± 0.2 | Ash-violet | Violet |
| 4 | 9.7 ± 0.2 | Violet-ash | Dark blue |
| 5 | 9.7 ± 0.2 | Red | Bright red |

What is claimed is:

1. At least one compound of formula (I), or at least one acid addition salt thereof or a mixture thereof:

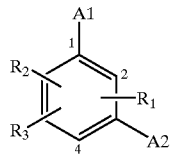

(I)

in which:

$R_1$, $R_2$ and $R_3$, which may be identical or different, are each chosen from hydrogen; halogens; Z groups; —CO—Z groups; —CO—OZ groups; ($C_1$–$C_6$) alkylcarbonyl groups; amino($C_1$–$C_6$)alkylcarbonyl groups; N—Z-amino($C_1$–$C_6$)alkylcarbonyl groups; N—($C_1$–$C_6$)alkylamino($C_1$–$C_6$)alkylcarbonyl groups; N,N-di($C_1$–$C_6$)alkylamino($C_1$–$C_6$)alkylcarbonyl groups; amino($C_1$–$C_6$)alkylcarbonyl($C_1$–$C_6$)alkyl groups; N—Z-amino($C_1$–$C_6$)alkylcarbonyl($C_1$–$C_6$) alkyl groups; N—($C_1$–$C_6$)alkylamino($C_1$–$C_6$)- alkylcarbonyl($C_1$–$C_6$)alkyl groups; N,N-di($C_1$–$C_6$) alkylamino($C_1$–$C_6$)alkylcarbonyl-($C_1$–$C_6$)alkyl groups; a carboxyl group; ($C_1$–$C_6$)alkylcarboxyl groups; $C_1$–$C_6$ alkylsulphonyl groups; aminosulphonyl groups; N—Z-aminosulphonyl groups; $C_1$–$C_6$ N-alkyl-aminosulphonyl groups; N,N-di($C_1$–$C_6$) alkylaminosulphonyl groups; $C_1$–$C_6$ aminosulphonylalkyl groups; $C_1$–$C_6$ N—Z-aminosulphonylalkyl groups; N—($C_1$–$C_6$)alkylaminosulphonyl($C_1$–$C_6$)alkyl groups; N,N-di($C_1$–$C_6$)alkylaminosulphonyl($C_1$–$C_6$) alkyl groups; a carbamyl group; N—($C_1$–$C_6$) alkylcarbamyl groups; N,N-di($C_1$–$C_6$)alkylcarbamyl groups; carbamyl($C_1$–$C_6$)alkyl groups; N—($C_1$–$C_6$) alkylcarbamyl($C_1$–$C_6$)alkyl groups; N,N-di($C_1$–$C_6$) alkylcarbamyl($C_1$–$C_6$)alkyl groups; $C_1$–$C_6$ alkyl groups; $C_1$–$C_6$ monohydroxyalkyl groups; $C_2$–$C_6$ polyhydroxyalkyl groups; ($C_1$–$C_6$)alkoxy($C_1$–$C_6$)alkyl groups; $C_1$–$C_6$ trifluoroalkyl groups; a cyano group; groups —$OR_6$; groups —$SR_6$; and amino groups protected With at least one group chosen from ($C_1$–$C_6$) alkylcarbonyl groups, ($C_1$–$C_6$)alkylcarboxyl groups, trifluoro($C_1$–$C_6$)alkylcarbonyl groups, amino($C_1$–$C_6$) alkylcarbonyl groups, N—Z-amino($C_1$–$C_6$) alkylcarbonyl groups, N—($C_1$–$C_6$)alkylamino($C_1$–$C_6$) alkylcarbonyl groups, N,N-di($C_1$–$C_6$)alkylamino ($C_1$–$C_6$)alkylcarbonyl groups, ($C_1$–$C_6$)alkylcarboxyl groups, a carbamyl group, N—($C_1$–$C_6$)alkylcarbamyl groups, N,N-di($C_1$–$C_6$)alkylcarbamyl groups, $C_1$–$C_6$ alkylsulphonyl groups, aminosulphonyl groups, N—Z-aminosulphonyl groups, $C_1$–$C_6$ N-alkylaminosulphonyl groups, N,N-di($C_1$–$C_6$) alkylaminosulphonyl groups, a thiocarbamyl group, a formyl group, —CO—Z groups, and —CO—OZ groups;

$R_6$ is chosen from $C_1$–$C_6$ alkyl groups; $C_1$–$C_6$ monohydroxyalkyl groups; $C_2$–$C_6$ polyhydroxyalkyl groups; groups Z;($C_1$–$C_6$)alkoxy($C_1$–$C_6$)alkyl groups: aryl groups; a benzyl group; carboxy($C_1$–$C_6$)alkyl groups; ($C_1$–$C_6$)alkylcarboxy-($C_1$–$C_6$)alkyl groups; cyano ($C_1$–$C_6$)alkyl groups; carbamyl($C_1$–$C_6$)alkyl groups; N—($C_1$–$C_6$)alkylcarbamyl($C_1$–$C_6$)alkyl groups; N,N-di($C_1$–$C_6$)alkylcarbamyl($C_1$–$C_6$)alkyl groups; $C_1$–$C_6$ trifluoroalkyl groups; $C_1$–$C_6$ aminosulphonylalkyl groups; $C_1$–$C_6$ N—Z-aminosulphonylalkyl groups; N—($C_1$–$C_6$)alkylaminosulphonyl($C_1$–$C_6$)alkyl groups; N,N-di($C_1$–$C_6$)alkylaminosulphonyl($C_1$–$C_6$)alkyl groups;($C_1$–$C_6$)alkylsulphinyl($C_{1-C_6}$)alkyl groups; ($C_1$–$C_6$)alkylsulphonyl($C_1$–$C_6$)alkyl groups; ($C_1$–$C_6$) alkylcarbonyl($C_1$–$C_6$)alkyl groups; $C_1$–$C_6$ aminoalkyl groups; $C_1$–$C_6$ aminoalkyl groups wherein said amino is substituted with one or two groups chosen from $C_1$–$C_6$ alkyl groups, $C_1$–$C_6$ monohydroxyalkyl groups, $C_2$–$C_6$ polyhydroxyalkyl groups, ($C_1$–$C_6$) alkylcarbonyl groups, a formyl group, trifluoro- ($C_1$–$C_6$)alkylcarbonyl groups, ($C_1$–$C_6$)alkylcarboxyl groups, a carbamyl group, N—($C_1$–$C_6$)alkylcarbamyl groups, N,N-di-($C_1$–$C_6$)alkylcarbamyl groups, a thiocarbamyl group, $C_1$–$C_6$ alkylsulphonyl groups, Z groups, —CO—Z groups, and —CO—OZ groups;

A1 is chosen from —$NR_4R_5$ groups and a hydroxyl group;

A2 is chosen from —$NR{=}_4R{=}_5$ groups and a hydroxyl group;

$R_4$, $R_5$, $R{=}_4$ and $R{=}_5$, which may be identical or different, are each chosen from hydrogen; Z groups; $C_1$–$C_6$ alkyl groups; $C_1$–$C_6$ monohydroxyalkyl groups; $C_2$–$C_6$ polyhydroxyalkyl groups;($C_1$–$C_6$)alkoxy ($C_1$–$C_6$)alkyl groups; aryl groups; a benzyl group; cyano($C_1$–$C_6$)alkyl groups; carbamyl($C_1$–$C_6$)alkyl groups; N—($C_1$–$C_6$)alkylcarbamyl($C_1$–$C_6$)alkyl groups; N,N-di($C_1$–$C_6$)alkylcarbamyl($C_1$–$C_6$)alkyl groups; thiocarbamyl($C_1$–$C_6$)alkyl groups; $C_1$–$C_6$ trifluoroalkyl groups; $C_1$–$C_6$ sulphoalkyl groups; ($C_1$–$C_6$) alkylcarboxy($C_1$–$C_6$)alkyl groups;($C_1$–$C_6$) alkylsulphinyl($C_1$–$C_6$)alkyl groups; $C_1$–$C_6$ aminosulphonylalkyl groups; $C_1$–$C_6$ N—Z-aminosulphonylalkyl groups; N—($C_1$–$C_6$) alkylaminosulphonyl($C_1$–$C_6$)alkyl groups; N,N-di ($C_1$–$C_6$)alkylaminosulphonyl($C_1$–$C_6$)alkyl groups; ($C_1$–$C_6$)alkylcarbonyl($C_1$–$C_6$)alkyl groups; $C_1$–$C_6$ aminoalkyl groups; $C_1$–$C_6$ aminoalkyl groups wherein said amino is substituted with one or two groups chosen from $C_1$–$C_6$ alkyl groups, $C_1$–$C_6$ monohydroxyalkyl groups, $C_2$–$C_6$ polyhydroxyalkyl groups, ($C_1$–$C_6$) alkylcarbonyl groups, a carbamyl group, N—($C_1$–$C_6$) alkylcarbamyl groups, N,N-di($C_1$–$C_6$)alkylcarbamyl groups, $C_1$–$C_6$ alkylsulphonyl groups, a formyl group, trifluoro($C_1$–$C_6$)alkylcarbonyl groups, ($C_1$–$C_6$) alkylcarboxyl groups, thiocarbamyl groups, Z groups, —CO—Z groups, and —CO—OZ groups;

one and only one of the groups $R_4$, $R{=}_4$, $R_5$ and $R{=}_5$ may also be chosen from($C_1$–$C_6$)alkylcarboxyl groups; ($C_1$–$C_6$)alkylcarbonyl groups; a formyl group; trifluoro ($C_1$–$C_6$)alkylcarbonyl groups; amino($C_1$–$C_6$) alkylcarbonyl groups; N—Z-amino($C_1$–$C_6$) alkylcarbonyl groups; N—($C_1$–$C_6$)alkylamino($C_1$–$C_6$) alkylcarbonyl groups; N,N-di($C_1$–$C_6$)alkylamino ($C_1$–$C_6$)alkylcarbonyl groups; a carbamyl group; N—($C_1$–$C_6$)alkylcarbamyl groups; N,N-di($C_1$–$C_6$) alkylcarbamyl groups; a thiocarbamyl group; an aminosulphonyl group; N—Z-aminosulphonyl groups;

N—($C_1$–$C_6$)alkylaminosulphonyl groups; N,N-di($C_1$–$C_6$)alkylaminosulphonyl groups; ($C_1$–$C_6$)alkylsulphonyl groups; —CO—Z groups; and —CO—OZ groups;

Z, which may be identical or different, is chosen from unsaturated cationic groups of formula (II), unsaturated cationic groups of formula (III), and saturated cationic groups of formula (IV):

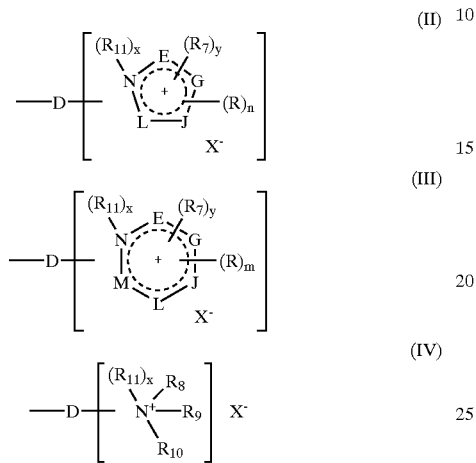

in which:
- D is a linker arm chosen form linear and branched divalent alkyl chains, wherein said linear and branched divalent alkyl chains can be interrupted by at least one heteroatom, and further wherein said linear and branched divalent alkyl chains can be substituted with at least one group chosen from a hydroxyl group and $C_1$–$C_6$ alkoxy groups;
- ring members E, G, J, L and M, which may be identical or different, are each chosen from carbon, oxygen, sulphur, and nitrogen;
- n is an integer chosen from 0 to 4 inclusive;
- m is an integer chosen from 0 to 5 inclusive;
- the groups R, which may be identical or different, are each chosen from additional Z groups which may be identical to or different from other Z groups, halogens, hydroxyl groups, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri($C_1$–$C_6$)alkylsilane($C_1$–$C_6$) alkyl groups, an amido group, an aldehydo group, a carboxyl group, ($C_1$–$C_6$)alkylcarbonyl groups, a thio group, $C_1$–$C_6$ thioalkyl groups, $C_1$–$C_6$ alkylthio groups, an amino group, amino groups protected with at least one group chosen from ($C_1$–$C_6$)alkylcarbonyl groups, a carbamyl group, and $C_1$–$C_6$ alkylsulphonyl groups, and NHR= groups and NR= R= groups wherein R= and R=, which may be identical or different, are each chosen from $C_1$–$C_6$ alkyl groups, $C_1$–$C_6$ monohydroxyalkyl groups and $C_2$–$C_6$ polyhydroxyalkyl groups;
- when n is greater than or equal to 2, two of the adjacent R groups may also form together an unsaturated ring chosen from 5- and 6-membered carbon-based rings and rings containing at least one hetero atom;
- $R_7$ is chosen from $C_1$–$C_6$, alkyl groups, $C_1$–$C_6$ monohydroxyalkyl groups, $C_1$–$C_6$ polyhydroxyalkyl groups, cyano($C_1$–$C_6$)alkyl groups, tri($C_1$–$C_6$)alkylsilane($C_1$–$C_6$)alkyl groups, ($C_1$–$C_6$)alkoxy($C_1$–$C_6$)alkyl groups, carbamyl-($C_1$–$C_6$)alkyl groups, ($C_1$–$C_6$)alkylcarboxy($C_1$–$C_6$)-alkyl groups, and a benzyl group;
- $R_8$, $R_9$ and $R_{10}$, which may be identical or different, are each chosen from $C_1$–$C_6$ alkyl groups, $C_1$–$C_6$ monohydroxyalkyl groups, $C_2$–$C_6$ polyhydroxyalkyl groups, ($C_1$–$C_6$)alkoxy($C_1$–$C_6$)alkyl groups, cyano($C_1$–$C_6$)alkyl groups, aryl groups, a benzyl group, $C_1$–$C_6$ amidoalkyl groups, tri($C_1$–$C_6$)alkylsilane($C_1$–$C_6$)alkyl groups, and $C_1$–$C_6$ aminoalkyl groups wherein said amino is protected with at least one group chosen from ($C_1$–$C_6$)alkylcarbonyl groups, a carbamyl group and $C_1$–$C_6$ alkylsulphonyl groups; two of said groups $R_8$, $R_9$ and $R_{10}$ can together optionally form, with the nitrogen atom to which they are attached, a saturated ring chosen from 5- and 6-membered carbon-based rings containing at least one heteroatom, wherein said ring is optionally substituted with at least one group chosen from halogens, a hydroxyl group, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri($C_1$–$C_6$)alkylsilane($C_1$–$C_6$)alkyl groups, an amido group, an aldehydo group, a carboxyl group, keto ($C_1$–$C_6$)alkyl groups, a thio group, $C_1$–$C_6$ thioalkyl groups, $C_1$–$C_6$ alkylthio groups, an amino group, and amino groups protected with at least one group chosen from ($C_1$–$C_6$)alkylcarbonyl groups, a carbamyl group and $C_1$–$C_6$ alkylsulphonyl groups;
- $R_{11}$ is chosen from $C_1$–$C_6$ alkyl groups, $C_1$–$C_6$ monohydroxyalkyl groups, $C_2$–$C_6$ polyhydroxyalkyl groups, aryl groups, a benzyl group, $C_1$–$C_6$ aminoalkyl groups, carboxy($C_1$–$C_6$)alkyl groups, cyano($C_1$–$C_6$)alkyl groups, carbamyl($C_1$–$C_6$)alkyl groups, $C_1$–$C_6$ trifluoroalkyl groups, tri($C_1$–$C_6$alkylsilane($C_1$–$C_6$)alkyl groups, $C_1$–$C_6$ sulphonamidoalkyl groups, ($C_1$–$C_6$)alkylcarboxyl($C_1$–$C_6$)alkyl groups, ($C_1$–$C_6$)alkylsulphinyl($C_1$–$C_6$)alkyl groups, ($C_1$–$C_6$)alkylsulphonyl($C_1$–$C_6$)alkyl groups, ($C_1$–$C_6$)alkylketo($C_1$–$C_6$)alkyl groups, N—($C_1$–$C_6$)alkylcarbamyl($C_1$–$C_6$)alkyl groups, N—($C_1$–$C_6$)alkylsulphonamido($C_1$–$C_6$)alkyl groups, and $C_1$–$C_6$ aminoalkyl groups wherein said amino is protected with at least one group chosen from ($C_1$–$C_6$) alkylcarbonyl groups, a carbamyl group and $C_1$–$C_6$ alkylsulphonyl groups; and
- x and y, which may be identical or different, are integers chosen from 0 and 1;
- x is chosen from a monovalent anion and a divalent anion; and provided that:
  when Z is an unsaturated cationic group of formula (II):
  - if x=0, then said linker arm D is attached to said nitrogen atom other, than E, G, J, and L,
  - if x=1, then said linker arm D is attached to one of said ring members chosen from E, G, J and L,
  - y=1 only when:
    1) said ring members E, G, J, and L are all simultaneously carbon atoms and $R_7$ is attached to said nitrogen atom of the unsaturated ring; or alternatively
    2) at least one of the ring members E, G, J, and L is a nitrogen atom to which $R_7$ is attached;
  when Z is an unsaturated cationic group of formula (III):

if x=0, then said linker arm D is attached to said nitrogen atom other than E, G, J, L, and M, if x=1, then said linker arm D is attached to one of said ring members chosen from E, G, J, L, and M, y=1 only when at least one of said ring members E, G, J, L and M is a divalent atom and $R_7$ is attached to said nitrogen atom of the unsaturated ring other than E, G, J, L and M ; and when Z is a cationic group of formula (IV):

if x=0, then the linker arm D is attached to the nitrogen atom bearing said groups $R_8$, $R_9$ and $R_{10}$;

if x=1, then two of said groups $R_8$, $R_9$ and $R_{10}$ form, together with the nitrogen atom to which they are attached, a saturated ring chosen from a 5- and 6-membered rings as defined above, and said linker arm D is attached to a carbon atom of said saturated ring;

wherein in said compound of formula (I), at least one of $R_1$, $R_2$, $R_3$, A1, and A2 comprises at least one Z group; and said compound of formula (I) excludes the compound of the following formula:

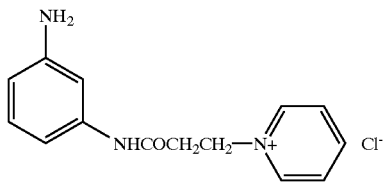

2. At least one compound, salt, or mixture thereof according to claim 1, wherein said linear and branched alkyl chains recited for D contain from 1 to 14 carbon atoms.

3. At least one compound, salt, or mixture thereof according to claim 1, wherein said at least one heteroatom recited for D is chosen from oxygen, nitrogen, and sulphur.

4. At least one compound, salt, or mixture according to claim 1, wherein said ring of said unsaturated cationic groups Z of formula (II) is chosen from a pyrrole ring, an imidazole ring, a pyrazole ring, an oxazole ring, an thiazole ring, a triazole ring, pyrazolopyrimidinium ring, a pyrazolopyridinium ring, a benzoimidazolinium ring, a bezoxazolinium ring, a benzothiazolinium ring, an indolinium ring, an indolidinium ring, an isoindolinium ring, an indazolinium ring, a benzotriazolinium ring, a benzoimidazolidinium ring and a benzopyrimidinium ring.

5. At least one compound, salt, or mixture according to claim 1, wherein said ring of said unsaturated cationic groups Z of formula (III) is chosen from a pyridine ring, a pyrimidine ring, a pyrazine ring, an oxazine ring, a triazine ring, a pyrazolopyrimidinium ring, a pyrazolopyridinium ring, a quinolinium ring and a tetrahydroquinolinium ring.

6. At least one compound, salt, or mixture according to claim 1, wherein two of said groups $R_8$, $R_9$ and $R_{10}$ form a ring chosen from a pyrrolidine ring, a piperidine ring, a piperazine ring and a morpholine ring.

7. At least one compound, salt, or mixture according to claim 1, wherein said X is chosen from halogens, a hydroxide group, a hydrogen sulphate group and a $C_1-C_6$ alkyl sulphate group.

8. At least one compound chosen from:

1-[3-(2,4-diaminophenoxy)propyl]-3-methyl-3H-imidazol-1-ium chloride;

1-[(3-hydroxy-4-methylphenylcarbamoyl)methyl]-3-methyl-3H-imidazol-1-ium chloride;

3-ethyl-1-[(3-hydroxyphenylcarbamoyl)methyl]-3H-imidazol-1-ium chloride;

1-[(3-hydroxy-2,4-dimethylphenylcarbamoyl)methyl]-3-methyl-3H-imidazol-1-ium chloride;

1-[(4-chloro-3-hydroxyphenylcarbamoyl)methyl]-3-methyl-3H-imidazol-1-ium chloride;

1-[(3-hydroxy-4-methoxyphenylcarbamoyl)methyl]-3-methyl-3H-imidazol-1-ium chloride;

1-[(3-hydroxy-4-methylphenylcarbamoyl)methyl]-2-methyl-2H-pyrazol-1-ium chloride;

1-[2-(3-hydroxy-4-methylphenylamino)ethyl]-3-methyl-3H-imidazol-1-ium bromide;

1-[2-(3-hydroxy-4-methylphenylcarbamoyloxy)ethyl]-2,3-dimethyl-3H-imidazol-1-ium chloride;

1-{[3-amino-4-(3-(3-methyl-3H-imidazol-1-ium)propoxy)phenylcarbamoyl]methyl}-3-methyl-3H-imidazol-1-ium dichloride;

3-(3-trimethylammonium-2-hydroxypropyl)-1-[(3-hydroxy-4-methylphenylcarbamoyl)methyl]-3H-imidazol-1-ium dichloride;

1-{[2-(2-(2,4-diaminophenoxy)ethylcarbamoyl]methyl}-3-methyl-3H-imidazol-1-ium chloride;

1-[(2,4-dihydroxyphenylcarbamoyl)methyl]-3-methyl-3H-imidazol-1-ium chloride;

N,N-bis[2-(3-methyl-3H-imidazol-1 -ium)ethyl]benzene-1,3-diamine dichloride;

1-{3-[4-amino-2-(2-triethylammoniumacetylamino)phenoxy]propyl}-3-methyl-3H-imidazol-1-ium dichloride;

1-(3-{4-amino-2-[2-(3-methyl-3H-imidazol-1-ium)acetylamino]phenoxy}propyl)-1,4-dimethylpiperazin-1-ium dichloride;

1-[2-(2,4-dihydroxyphenyl)-2-oxoethyl]-3-methyl-3H-imidazol-1-ium chloride;

1-[2-(2,4-diaminophenyl)ethyl]-3-methyl-3H-imidazol-1-ium chloride; or at least one acid addition salt thereof; or a mixture thereof.

9. A compound according to claim 1, wherein said acid addition salt is chosen from a hydrochloride, a hydrobromide, a sulphate, a citrate, a succinate, a tartrate, a lactate and an acetate.

10. At least one coupler for oxidation dyeing of keratin fibres chosen from compounds of formula (I) and acid addition salts thereof:

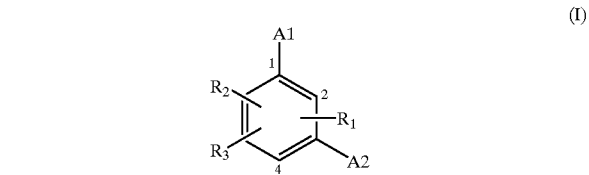

in which:

$R_1$, $R_2$ and $R_3$, which may be identical or different, are each chosen from hydrogen; halogens; Z groups; —CO—Z groups; —CO—OZ groups; $(C_1-C_6)$ alkylcarbonyl groups; amino$(C_1-C_6)$alkylcarbonyl groups; N—Z-amino$(C_1-C_6)$alkylcarbonyl groups; N—$(C_1-C_6)$alkylamino$(C_1-C_6)$alkylcarbonyl groups; N,N-di$(C_1-C_6)$alkylamino$(C_1-C_6)$alkylcarbonyl groups; amino$(C_1-C_6)$alkylcarbonyl$(C_1-C_6)$alkyl groups; N—Z-amino$(C_1-C_6)$alkylcarbonyl$(C_1-C_6)$alkyl groups; N—$(C_1-C_6)$alkylamino$(C_1-C_6)$-alkylcarbonyl$(C_1-C_6)$alkyl groups; N,N-di$(C_1-C_6)$alkylamino$(C_1-C_6)$alkylcarbonyl-$(C_1-C_6)$alkyl groups; a carboxyl group; $(C_1-C_6)$alkylcarboxyl groups; $C_1-C_6$ alkylsulphonyl groups; aminosulphonyl groups; N—Z-aminosulphonyl groups; $C_1-C_6$ N-alkylaminosulphonyl groups; N,N-di$(C_1-C_6)$ alkylaminosulphonyl groups; $C_1-C_6$ aminosulphonylalkyl groups; $C_1-C_6$ N—Z-aminosulphonylalkyl groups; N—$(C_1-C_6)$alkylaminosulphonyl$(C_1-C_6)$alkyl groups; N,N-di$(C_1-C_6)$alkylaminosulphonyl$(C_1-C_6)$ alkyl groups; a carbamyl group; N—$(C_1-C_6)$ alkylcarbamyl groups; N,N-di$(C_1-C_6)$alkylcarbamyl groups; carbamyl$(C_1-C_6)$alkyl groups; N—$(C_1-C_6)$ alkylcarbamyl$(C_1-C_6)$alkyl groups; N,N-di$(C_1-C_6)$ alkylcarbamyl$(C_1-C_6)$alkyl groups; $C_1-C_6$ alkyl groups; $C_1-C_6$ monohydroxyalkyl groups; $C_2-C_6$ polyhydroxyalkyl groups; $(C_1-C_6)$alkoxy$(C_1-C_6)$alkyl groups; $C_1-C_6$ trifluoroalkyl groups; a cyano group; groups —$OR_6$; groups —$SR_6$; and amino groups protected with at least one group chosen from $(C_1-C_6)$ alkylcarbonyl groups, $(C_1-C_6)$alkylcarboxyl groups, trifluoro$(C_1-C_6)$alkylcarbonyl groups, amino$(C_1-C_6)$ alkylcarbonyl groups, N—Z-amino$(C_1-C_6)$ alkylcarbonyl groups, N—$(C_1-C_6)$alkylamino$(C_1-C_6)$ alkylcarbonyl groups, N,N-di$(C_1-C_6)$alkylamino $(C_1-C_6)$alkylcarbonyl groups, $(C_1-C_6)$alkylcarboxyl groups, a carbamyl group, N—$(C_1-C_6)$alkylcarbamyl groups, N,N-di$(C_1-C_6)$alkylcarbamyl groups, $C_1-C_6$ alkylsulphonyl groups, aminosulphonyl groups, N-Z-aminosulphonyl groups, $C_1-C_6$ N-alkylaminosulphonyl groups, N,N-di$(C_1-C_6)$ alkylaminosulphonyl groups, a thiocarbamyl group, a formyl group, —CO—Z groups, and —CO—OZ groups;

$R_6$ is chosen from $C_1-C_6$ alkyl groups; $C_1-C_6$ monohydroxyalkyl groups; $C_2-C_6$ polyhydroxyalkyl groups; groups Z; $(C_1-C_6)$alkoxy$(C_1-C_6)$alkyl groups; aryl groups; a benzyl group; carboxy$(C_1-C_6)$alkyl groups; $(C_1-C_6)$alkylcarboxy-$(C_1-C_6)$alkyl groups; cyano$(C_1-C_6)$alkyl groups; carbamyl$(C_1-C_6)$alkyl groups; N—$(C_1-C_6)$alkylcarbamyl$(C_1-C_6)$alkyl groups; N,N-di$(C_1-C_6)$alkylcarbamyl$(C_1-C_6)$alkyl groups; $C_1-C_6$ trifluoroalkyl groups; $C_1-C_6$ aminosulphonylalkyl groups; $C_1-C_6$ N—Z-aminosulphonylalkyl groups; N—$(C_1-C_6)$alkylaminosulphonyl$(C_1-C_6)$alkyl groups; N,N-di$(C_1-C_6)$alkylaminosulphonyl$(C_1-C_6)$alkyl groups; $(C_1-C_6)$alkylsulphinyl$(C_1-C_6)$alkyl groups; $(C_1-C_6)$alkylsulphonyl$(C_1-C_6)$alkyl groups; $(C_1-C_6)$alkylcarbonyl$(C_1-C_6)$alkyl groups; $C_1-C_6$aminoalkyl groups; $C_1-C_6$ aminoalkyl groups wherein said amino is substituted with one or two groups chosen from $C_1-C_6$ alkyl groups, $C_1-C_6$ monohydroxyalkyl groups, $C_2-C_6$polyhydroxyalkyl groups, $(C_1-C_6)$alkylcarbonyl groups, a formyl group, trifluoro-$(C_1-C_6)$alkylcarbonyl groups, $(C_1-C_6)$alkylcarboxyl groups, a carbamyl group, N—$(C_1-C_6)$alkylcarbamyl groups, N,N-di $(C_1-C_6)$alkylcarbamyl groups, a thiocarbamyl group, $C_1-C_6$ alkylsulphonyl groups, Z groups, —CO—Z groups, and —CO—OZ groups;

A1 is chosen from —$NR_4R_5$ groups and a hydroxyl group;

A2 is chosen from —$NR=_4R=_5$ groups and a hydroxyl group;

$R_4$, $R_5$, $R=_4$ and $R=_5$, which may be identical or different, are each chosen from hydrogen; Z groups; $C_1-C_6$ alkyl groups; $C_1-C_6$ monohydroxyalkyl groups; $C_2-C_6$ polyhydroxyalkyl groups; $(C_1-C_6)$alkoxy $(C_1-C_6)$alkyl groups; aryl groups; a benzyl group; cyano$(C_1-C_6)$alkyl groups; carbamyl$(C_1-C_6)$alkyl groups; N—$(C_1-C_6)$alkylcarbamyl$(C_1-C_6)$alkyl groups; N,N-di$(C_1-C_6)$alkylcarbamyl$(C_1-C_6)$alkyl groups; thiocarbamyl$(C_1-C_6)$alkyl groups; $C_1-C_6$ trifluoroalkyl groups; $C_1-C_6$ sulphoalkyl groups; $(C_1-C_6)$ alkylcarboxy$(C_1-C_6)$alkyl groups; $(C_1-C_6)$ alkylsulphinyl$(C_1-C_6)$alkyl groups; $C_1-C_6$ aminosulphonylalkyl groups; $C_1-C_6$ N—Z-aminosulphonylalkyl groups; N—$(C_1-C_6)$ alkylaminosulphonyl$(C_1-C_6)$alkyl groups; N,N-di $(C_1-C_6)$alkylaminosulphonyl$(C_1-C_6)$alkyl groups; $(C_1-C_6)$alkylcarbonyl$(C_1-C_6)$alkyl groups; $C_1-C_6$ aminoalkyl groups; $C_1-C_6$ aminoalkyl groups wherein said amino is substituted with one or two groups chosen from $C_1-C_6$ alkyl groups, $C_1-C_6$ monohydroxyalkyl groups, $C_2-C_6$ polyhydroxyalkyl groups, $(C_1-C_6)$ alkylcarbonyl groups, a carbamyl group, N—$(C_1-C_6)$ alkylcarbamyl groups, N,N-di$(C_1-C_6)$alkylcarbamyl groups, $C_1-C_6$ alkylsulphonyl groups, a formyl group, trifluoro$(C_1-C_6)$alkylcarbonyl groups, $(C_1-C_6)$ alkylcarboxyl groups, thiocarbamyl groups, Z groups, —CO—Z groups, and —CO—OZ groups;

one and only one of the groups $R_4$, $R=_4$, $R_5$ and $R=_5$ may also be chosen from$(C_1-C_6)$alkylcarboxyl groups; $(C_1-C_6)$alkylcarbonyl groups; a formyl group; trifluoro $(C_1-C_6)$alkylcarbonyl groups; amino$(C_1-C_6)$ alkylcarbonyl groups; N—Z-amino$(C_1-C_6)$ alkylcarbonyl groups; N—$(C_1-C_6)$alkylamino$(C_1-C_6)$ alkylcarbonyl groups; N,N-di$(C_1-C_6)$alkylamino $(C_1-C_6)$alkylcarbonyl groups; a carbamyl group; N—$(C_1-C_6)$alkylcarbamyl groups; N,N-di$(C_1-C_6)$ alkylcarbamyl groups; a thiocarbamyl group; an aminosulphonyl group; N—Z-aminosulphonyl groups; N—$(C_1-C_6)$alkylaminosulphonyl groups; N,N-di $(C_1-C_6)$alkylaminosulphonyl groups; $(C_1-C_6)$ alkylsulphonyl groups; —CO—Z groups; and —CO—OZ groups;

Z, which may be identical or different, is chosen from unsaturated cationic groups of formula (II), unsaturated cationic groups of formula (III), and saturated cationic groups of formula (IV):

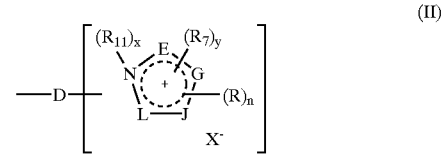

(II)

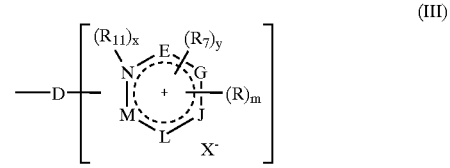

(III)

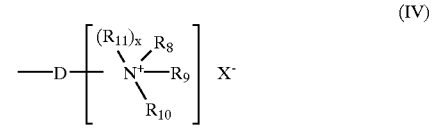

(IV)

in which:

D is a linker arm chosen form linear and branched divalent alkyl chains, wherein said linear and branched divalent alkyl chains can be interrupted by at least one heteroatom, and further wherein said linear and branched divalent alkyl chains can be substituted with at least one group chosen from a hydroxyl group and $C_1-C_6$ alkoxy groups;

ring members E, G, J, L and M, which may be identical or different, are each chosen from carbon, oxygen, sulphur, and nitrogen;

n is an integer chosen from 0 to 4 inclusive;

m is an integer chosen from 0 to 5 inclusive;

the groups R, which may be identical or different, are each chosen from additional Z groups which may be identical to or different from other Z groups, halogens, hydroxyl groups, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri($C_1$–$C_6$)alkylsilane($C_1$–$C_6$)alkyl groups, an amido group, an aldehydo group, a carboxyl group, ($C_1$–$C_6$) alkylcarbonyl groups, a thio group, $C_1$–$C_6$, thioalkyl groups, $C_1$–$C_6$ alkylthio groups, an amino group, amino groups protected with at least one group chosen from ($C_1$–$C_6$)alkylcarbonyl groups, a carbamyl group, and $C_1$–$C_6$ alkylsulphonyl groups, and NHR= groups and NR= R= groups wherein R= and R=, which may be identical or different, are each chosen from $C_1$–$C_6$ alkyl groups, $C_1$–$C_6$ monohydroxyalkyl groups and $C_2$–$C_6$ polyhydroxyalkyl groups;

when n is greater than or equal to 2, two of the adjacent R groups may also form together an unsaturated ring chosen from 5- and 6-membered carbon-based rings and rings containing at least one hetero atom;

$R_7$ is chosen from $C_1$–$C_6$ alkyl groups, $C_1$–$C_6$ monohydroxyalkyl groups, $C_2$–$C_6$ polyhydroxyalkyl groups, cyano($C_1$–$C_6$)alkyl groups, tri($C_1$–$C_6$) alkylsilane($C_1$ –$C_6$)alkyl groups, ($C_1$–$C_6$)alkoxy ($C_1$–$C_6$)alkyl groups, carbamyl-($C_1$–$C_6$)alkyl groups, ($C_1$–$C_6$)alkylcarboxy($C_1$–$C_6$)-alkyl groups, and a benzyl group;

$R_8$, $R_9$ and $R_{10}$, which may be identical or different, are each chosen from $C_1$–$C_6$ alkyl groups, $C_1$–$C_6$ monohydroxyalkyl groups, $C_2$–$C_6$ polyhydroxyalkyl groups, ($C_1$–$C_6$)alkoxy($C_1$–$C_6$)alkyl groups, cyano ($C_1$–$C_6$)alkyl groups, aryl groups, a benzyl group, $C_1$–$C_6$ amidoalkyl groups, tri($C_1$–$C_6$)alkylsilane ($C_1$–$C_6$)alkyl groups, and $C_1$–$C_6$ aminoalkyl groups wherein said amino is protected with at least one group chosen from ($C_1$–$C_6$)alkylcarbonyl groups, a carbamyl group and $C_1$–$C_6$ alkylsulphonyl groups; two of said groups $R_8$, $R_9$ and $R_{10}$ can together optionally form, with the nitrogen atom to which they are attached, a saturated ring chosen from 5- and 6-membered carbon-based rings containing at least one heteroatom, wherein said ring is optionally substituted with at least one group chosen from halogens, a hydroxyl group, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri($C_1$–$C_6$)alkylsilane($C_1$–$C_6$)alkyl groups, an amido group, an aldehydo group, a carboxyl group, keto ($C_1$–$C_6$)alkyl groups, a thio group, $C_1$–$C_6$ thioalkyl groups, $C_1$–$C_6$ alkylthio groups, an amino group, and amino groups protected with at least one group chosen from ($C_1$–$C_6$)alkylcarbonyl groups, a carbamyl group and $C_1$–$C_6$ alkylsulphonyl groups;

$R_{11}$ is chosen from $C_1$–$C_6$ alkyl groups, $C_1$–$C_6$ monohydroxyalkyl groups, $C_2$–$C_6$ polyhydroxyalkyl groups, aryl groups, a benzyl group, $C_1$–$C_6$ aminoalkyl groups, carboxy($C_1$–$C_6$)alkyl groups, cyano ($C_1$–$C_6$)alkyl groups, carbamyl($C_1$–$C_6$)alkyl groups, $C_1$–$C_6$ trifluoroalkyl groups, tri($C_1$–$C_6$)alkylsilane ($C_1$–$C_6$)alkyl groups, $C_1$–$C_6$ sulphonamidoalkyl groups, ($C_1$–$C_6$)alkylcarboxy($C_1$–$C_6$)alkyl groups, ($C_1$–$C_6$)alkylsulphinyl($C_1$–$C_6$)alkyl groups, ($C_1$–$C_6$) alkylsulphonyl($C_1$–$C_6$)alkyl groups, ($C_1$–$C_6$) alkylketo($C_1$–$C_6$)alkyl groups, N—($C_1$–$C_6$) alkylcarbamyl($C_1$–$C_6$)alkyl groups, N—($C_1$–$C_6$) alkylsulphonamido($C_1$–$C_6$)alkyl groups, and $C_1$–$C_6$ aminoalkyl groups wherein said amino is protected with at least one group chosen from ($C_1$–$C_6$) alkylcarbonyl groups, a carbamyl group and $C_1$–$C_6$ alkylsulphonyl groups; and x and y, which may be Identical or different, are integers chosen from 0 and 1;

x⁻ is chosen from a monovalent anion and a divalent anion; and provided that:

when Z is an unsaturated cationic group of formula (II):

if x=0, then said linker arm D is attached to said nitrogen atom other than E, G, J, and L, if x=1, then said linker arm D is attached to one of said ring members chosen from E, G, J and L, y=1 only when:
1) said ring members E, G, J, and L are all simultaneously carbon atoms and $R_7$ is attached to said nitrogen atom of the unsaturated ring; or alternatively
2) at least one of the ring members E, G, J, and L is a nitrogen atom to which $R_7$ is attached;

when Z is an unsaturated cationic group of formula (III):

if x=0, then said linker arm D is attached to said nitrogen atom other than E, G, J, L, and M, if x=1, then said linker arm D is attached to one of said ring members chosen from E, G, J, L, and M, y=1 only when at least one of said ring members E, G, J, L and M is a divalent atom and $R_7$ is attached to said nitrogen atom of the unsaturated ring other than E, G, J, L and M ; and when Z is a cationic group of formula (IV):

if x=0, then the linker arm D is attached to the nitrogen atom bearing said groups $R_8$, $R_9$ and $R_{10}$;

if x=1, then two of said groups $R_8$, $R_9$ and $R_{10}$ form, together with the nitrogen atom to which they are attached, a saturated ring chosen from a 5- and 6-membered rings as defined above, and said linker arm D is attached to a carbon atom of said saturated ring;

wherein in said compound of formula (I), at least one of $R_1$, $R_2$, $R_3$, A1, and A2 comprises at least one Z group.

11. At least one coupler for oxidation dyeing of keratin fibres according to claim 10, wherein said keratin fibres are human keratin fibres.

12. At least one coupler for oxidation dyeing of keratin fibres according to claim 11, wherein said human keratin fibres are hair.

13. A composition for the oxidation dyeing of keratin fibres comprising, in a medium suitable for dyeing, at least one coupler chosen from compounds of formula (I) and acid addition salts thereof:

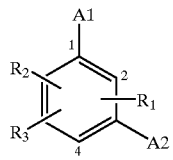
(I)

in which:

R$_1$, R$_2$ and R$_3$, which may be identical or different, are each chosen from hydrogen; halogens; Z groups; —CO—Z groups; —CO—OZ groups; (C$_1$–C$_6$) alkylcarbonyl groups; amino(C$_1$–C$_6$)alkylcarbonyl groups; N—Z-amino(C$_1$–C$_6$)alkylcarbonyl groups; N—(C$_1$–C$_6$)alkylamino(C$_1$–C$_6$)alkylcarbonyl groups; N,N-di(C$_1$–C$_6$)alkylamino(C$_1$–C$_6$)alkylcarbonyl groups; amino(C$_1$–C$_6$)alkylcarbonyl(C$_1$–C$_6$)alkyl groups; N—Z-amino(C$_1$–C$_6$)alkylcarbonyl(C$_1$–C$_6$) alkyl groups; N—(C$_1$–C$_6$)alkylamino(C$_1$–C$_6$)-alkylcarbonyl(C$_1$–C$_6$)alkyl groups; N,N-di(C$_1$–C$_6$) alkylamino(C$_1$–C$_6$)alkylcarbonyl-(C$_1$–C$_6$)alkyl groups; a carboxyl group; (C$_1$–C$_6$)alkylcarboxyl groups; C$_1$–C$_6$ alkylsulphonyl groups; aminosulphonyl groups; N—Z-aminosulphonyl groups; C$_1$–C$_6$ N-alkylaminosulphonyl groups; N,N-di(C$_1$–C$_6$) alkylaminosulphonyl groups; C$_1$–C$_6$ aminosulphonylalkyl groups; C$_1$–C$_6$ N—Z-aminosulphonylalkyl groups; N—(C$_1$–C$_6$)alkylaminosulphonyl(C$_1$–C$_6$)alkyl groups; N,N-di(C$_1$–C$_6$)alkylaminosulphonyl(C$_1$–C$_6$) alkyl groups; a carbamyl group; N—(C$_1$–C$_6$) alkylcarbamyl groups; N,N-di(C$_1$–C$_6$)alkylcarbamyl groups; carbamyl(C$_1$–C$_6$)alkyl groups; N—(C$_1$–C$_6$) alkylcarbamyl(C$_1$–C$_6$)alkyl groups; N,N-di(C$_1$–C$_6$) alkylcarbamyl(C$_1$–C$_6$)alkyl groups; C$_1$–C$_6$ alkyl groups; C$_1$–C$_6$ monohydroxyalkyl groups; C$_2$–C$_6$ polyhydroxyalkyl groups; (C$_1$–C$_6$)alkoxy(C$_1$–C$_6$)alkyl groups; C$_1$–C$_6$ trifluoroalkyl groups; a cyano group; groups —OR$_6$; groups —SR$_6$; and amino groups protected with at least one group chosen from (C$_1$–C$_6$) alkylcarbonyl groups, (C$_1$–C$_6$)alkylcarboxyl groups, trifluoro(C$_1$–C$_6$)alkylcarbonyl groups, amino(C$_1$–C$_6$) alkylcarbonyl groups, N—Z-amino(C$_1$–C$_6$) alkylcarbonyl groups, N—(C$_1$–C$_6$)alkylamino(C$_1$–C$_6$) alkylcarbonyl groups, N,N-di(C$_1$–C$_6$)alkylamino (C$_1$–C$_6$)alkylcarbonyl groups, (C$_1$–C$_6$)alkylcarboxyl groups, a carbamyl group, N—(C$_1$–C$_6$)alkylcarbamyl groups, N,N-di(C$_1$–C$_6$)alkylcarbamyl groups, C$_1$–C$_6$ alkylsulphonyl groups, aminosulphonyl groups, N—Z-aminosulphonyl groups, C$_1$–C$_6$ N-alkylaminosulphonyl groups, N,N-di(C$_1$–C$_6$) alkylaminosulphonyl groups, a thiocarbamyl group, a formyl group, —CO—Z groups, and —CO—OZ groups;

R$_6$ is chosen from C$_1$–C$_6$ alkyl groups; C$_1$–C$_6$ monohydroxyalkyl groups; C$_2$–C$_6$ polyhydroxyalkyl groups; groups Z; (C$_1$–C$_6$)alkoxy(C$_1$–C$_6$)alkyl groups; aryl groups; a benzyl group; carboxy(C$_1$–C$_6$)alkyl groups; (C$_1$–C$_6$)alkylcarboxyl-(C$_1$–C$_6$)alkyl groups; cyano(C$_1$–C$_6$)alkyl groups; carbamyl(C$_1$–C$_6$)alkyl groups; N—(C$_1$–C$_6$)alkylcarbamyl(C$_1$–C$_6$)alkyl groups; N,N-di(C$_{C6}$)alkylcarbamyl(C$_1$–C$_6$)alkyl groups; C$_1$–C$_6$ trifluoroalkyl groups; C$_1$–C$_6$ aminosulphonylalkyl groups; C$_1$–C$_6$ N—Z-aminosulphonylalkyl groups; N—(C$_1$–C$_6$)alkylaminosulphonyl(C$_1$–C$_6$)alkyl groups; N,N-di(C$_1$–C$_6$)alkylaminosulphonyl(C$_1$–C$_6$)alkyl groups; (C$_1$–C$_6$)alkylsulphinyl(C$_1$–C$_6$)alkyl groups; (C$_1$–C$_6$)alkylsulphonyl(C$_1$–C$_6$)alkyl groups; (C$_1$–C$_6$) alkylcarbonyl(C$_1$–C$_6$)alkyl groups; C$_1$–C$_6$ aminoalkyl groups; C$_1$–C$_6$ aminoalkyl groups wherein said amino is substituted with one or two groups chosen from C$_1$–C$_6$ alkyl groups, C$_1$–C$_6$ monohydroxyalkyl groups, C$_2$–C$_6$ polyhydroxyalkyl groups, (C$_1$–C$_6$) alkylcarbonyl groups, a formyl group, trifluoro-(C$_1$–C$_6$)alkylcarbonyl groups, (C$_1$–C$_6$)alkylcarboxyl groups, a carbamyl group, N—(C$_1$–C$_6$)alkylcarbamyl groups, N,N-di-(C$_1$–C$_6$)alkylcarbamyl groups, a thiocarbamyl group, C$_1$–C$_6$ alkylsulphonyl groups, Z groups, —CO—Z groups, and —CO—OZ groups;

A1 is chosen from —NR$_4$R$_5$ groups and a hydroxyl group;

A2 is chosen from —NR═$_4$R═$_5$ groups and a hydroxyl group;

R$_4$, R$_5$, R═$_4$ and R═$_5$, which may be identical or different, are each chosen from hydrogen; Z groups; C$_1$–C$_6$ alkyl groups; C$_1$–C$_6$ monohydroxyalkyl groups; C$_2$–C$_6$ polyhydroxyalkyl groups; (C$_1$–C$_6$)alkoxy (C$_1$–C$_6$)alkyl groups; aryl groups; a benzyl group; cyano(C$_1$–C$_6$)alkyl groups; carbamyl(C$_1$–C$_6$)alkyl groups; N—(C$_1$–C$_6$)alkylcarbamyl(C$_1$–C$_6$)alkyl groups; N,N-di(C$_1$–C$_6$)alkylcarbamyl(C$_1$–C$_6$)alkyl groups; thiocarbamyl(C$_1$–C$_6$)alkyl groups; C$_1$–C$_6$ trifluoroalkyl groups; C$_1$–C$_6$ sulphoalkyl groups; (C$_1$–C$_6$) alkylcarboxy(C$_1$–C$_6$)alkyl groups; (C$_1$–C$_6$) alkylsulphinyl(C$_1$–C$_6$)alkyl groups; C$_1$–C$_6$ aminosulphonylalkyl groups; C$_1$–C$_6$ N—Z-aminosulphonylalkyl groups; N—(C$_1$–C$_6$) alkylaminosulphonyl(C$_1$–C$_6$)alkyl groups; N,N-di (C$_1$–C$_6$)alkylaminosulphonyl(C$_1$–C$_6$)alkyl groups; (C$_1$–C$_6$)alkylcarbonyl(C$_1$–C$_6$)alkyl groups; C$_1$–C$_6$ aminoalkyl groups; C$_1$–C$_6$ aminoalkyl groups wherein said amino is substituted with one or two groups chosen from C$_1$–C$_6$ alkyl groups, C$_1$–C$_6$ monohydroxyalkyl groups, C$_2$–C$_6$ polyhydroxyalkyl groups, (C$_1$–C$_6$) alkylcarbonyl groups, a carbamyl group, N—(C$_1$–C$_6$) alkylcarbamyl groups, N,N-di(C$_1$–C$_6$)alkylcarbamyl groups, C$_1$–C$_6$ alkylsulphonyl groups, a formyl group, trifluoro(C$_1$–C$_6$)alkylcarbonyl groups, (C$_1$–C$_6$) alkylcarboxyl groups, thiocarbamyl groups, Z groups, —CO—Z groups, and —CO—OZ groups;

one and only one of the groups R$_4$, R═$_4$, R$_5$ and R═$_5$ may also be chosen from (C$_1$–C$_6$)alkylcarboxyl groups; (C$_1$–C$_6$)alkylcarbonyl groups; a formyl group; trifluoro (C$_1$–C$_6$)alkylcarbonyl groups; amino(C$_1$–C$_6$) alkylcarbonyl groups; N—Z-amino(C$_1$–C$_6$) alkylcarbonyl groups; N—(C$_1$–C$_6$)alkylamino(C$_1$–C$_6$) alkylcarbonyl groups; N,N-di(C$_1$–C$_6$)alkylamino (C$_1$–C$_6$)alkylcarbonyl groups; a carbamyl group; N—(C$_1$–C$_6$)alkylcarbamyl groups; N,N-di(C$_1$–C$_6$) alkylcarbamyl groups; a thiocarbamyl group; an aminosulphonyl group; N—Z-aminosulphonyl groups; N—(C$_1$–C$_6$)alkylaminosulphonyl groups; N,N-di (C$_1$–C$_6$)alkylaminosulphonyl groups; (C$_1$–C$_6$) alkylsulphonyl groups; —CO—Z groups; and —CO—OZ groups;

Z, which may be identical or different, is chosen from unsaturated cationic groups of formula (II), unsaturated cationic groups of formula (III), and saturated cationic groups of formula (IV):

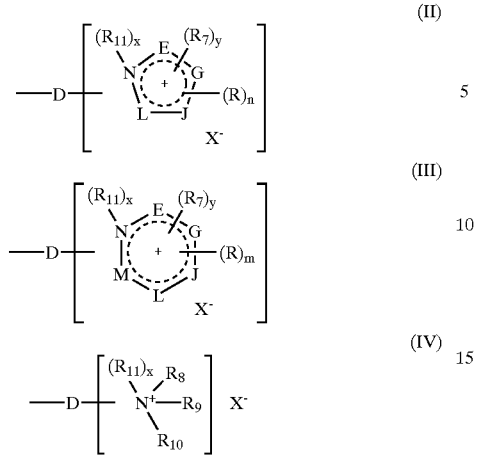

in which:
- D is a linker arm chosen form linear and branched divalent alkyl chains, wherein said linear and branched divalent alkyl chains can be interrupted by at least one heteroatom, and further wherein said linear and branched divalent alkyl chains can be substituted with at least one group chosen from a hydroxyl group and $C_1$–$C_6$ alkoxy groups;
- ring members E, G, J, L and M, which may be identical or different, are each chosen from carbon, oxygen, sulphur, and nitrogen;
- n is an integer chosen from 0 to 4 inclusive;
- m is an integer chosen from 0 to 5 inclusive;
- the groups R, which may be identical or different, are each chosen from additional Z groups which may be identical to or different from other Z groups, halogens, hydroxyl groups, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri($C_1$–$C_6$)alkylsilane($C_1$–$C_6$) alkyl groups, an amido group, an aldehydo group, a carboxyl group, ($C_1$–$C_6$)alkylcarbonyl groups, a thio group, $C_1$–$C_6$ thioalkyl groups, $C_1$–$C_6$ alkylthio groups, an amino group, amino groups protected with at least one group chosen from ($C_1$–$C_6$)alkylcarbonyl groups, a carbamyl group, and $C_1$–$C_6$ alkylsulphonyl groups, and NHR=== groups and NR=== R==== groups wherein R=== and R====, which may be identical or different, are each chosen from $C_1$–$C_6$ alkyl groups, $C_1$–$C_6$ monohydroxyalkyl groups and $C_1$–$C_6$ polyhydroxyalkyl groups;
- when n is greater than or equal to 2, two of the adjacent R groups may also form together an unsaturated ring chosen from 5- and 6-membered carbon-based rings and rings containing at least one hetero atom;
- $R_7$ is chosen from $C_1$–$C_6$ alkyl groups, $C_1$–$C_6$ monohydroxyalkyl groups, $C_1$–$C_6$ polyhydroxyalkyl groups, cyano($C_1$–$C_6$)alkyl groups, tri($C_1$–$C_6$)alkylsilane($C_1$–$C_6$)alkyl groups, ($C_1$–$C_6$)alkoxy($C_1$–$C_6$)alkyl groups, carbamyl-($C_1$–$C_6$)alkyl groups, ($C_1$–$C_6$)alkylcarboxy($C_1$–$C_6$)-alkyl groups, and a benzyl group;
- $R_8$, $R_9$ and $R_{10}$, which may be identical or different, are each chosen from $C_1$–$C_6$ alkyl groups, $C_1$–$C_6$ monohydroxyalkyl groups, $C_2$–$C_6$ polyhydroxyalkyl groups, ($C_1$–$C_6$)alkoxy($C_1$–$C_6$)alkyl groups, cyano ($C_1$–$C_6$)alkyl groups, aryl groups, a benzyl group, $C_1$–$C_6$ amidoalkyl groups, tri($C_1$–$C_6$)alkylsilane ($C_1$–$C_6$)alkyl groups, and $C_1$–$C_6$ aminoalkyl groups wherein said amino is protected with at least one group chosen from ($C_1$–$C_6$)alkylcarbonyl groups, a carbamyl group and $C_1$–$C_6$ alkylsulphonyl groups;
two of said groups $R_8$, $R_9$ and $R_{10}$ can together optionally form, with the nitrogen atom to which they are attached, a saturated ring chosen from 5- and 6-membered carbon-based rings containing at least one heteroatom, wherein said ring is optionally substituted with at least one group chosen from halogens, a hydroxyl group, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri($C_1$–$C_6$)alkylsilane($C_1$–$C_6$)alkyl groups, an amido group, an aldehydo group, a carboxyl group, keto ($C_1$–$C_6$)alkyl groups, a thio group, $C_1$–$C_6$ thioalkyl groups, $C_1$–$C_6$ alkylthio groups, an amino group, and amino groups protected with at least one group chosen from ($C_1$–$C_6$)alkylcarbonyl groups, a carbamyl group and $C_1$–$C_6$ alkylsulphonyl groups;
- $R_{11}$ is chosen from $C_1$–$C_6$ alkyl groups, $C_1$–$C_6$ monohydroxyalkyl groups, $C_2$–$C_6$ polyhydroxyalkyl groups, aryl groups, a benzyl group, $C_1$–$C_6$ aminoalkyl groups, carboxy($C_1$–$C_6$)alkyl groups, cyano ($C_1$–$C_6$)alkyl groups, carbamyl($C_1$–$C_6$)alkyl groups, $C_1$–$C_6$ trifluoroalkyl groups, tri($C_1$–$C_6$)alkylsilane ($C_1$–$C_6$)alkyl groups, $C_1$–$C_6$ sulphonamidoalkyl groups, ($C_1$–$C_6$)alkylcarboxy($C_1$–$C_6$)alkyl groups, ($C_1$–$C_6$)alkylsulphinyl($C_1$–$C_6$)alkyl groups, ($C_1$–$C_6$) alkylsulphonyl($C_1$–$C_6$)alkyl groups, ($C_1$–$C_6$) alkylketo($C_1$–$C_6$)alkyl groups, N—($C_1$–$C_6$) alkylcarbamyl($C_1$–$C_6$)alkyl groups, N—($C_1$–$C_6$) alkylsulphonamido($C_1$–$C_6$)alkyl groups, and $C_1$–$C_6$ aminoalkyl groups wherein said amino is protected with at least one group chosen from ($C_1$–$C_6$) alkylcarbonyl groups, a carbamyl group and $C_1$–$C_6$ alkylsulphonyl groups; and
- x and y, which may be identical or different, are integers chosen from 0 and 1;
- $X^-$ is chosen from a monovalent anion and a divalent anion; and provided that:
- when Z is an unsaturated cationic group of formula (II):
  - if x=0, then said linker arm D is attached to said nitrogen atom other than E, G, J, and L,
  - if x=1, then said linker arm D is attached to one of said ring members chosen from E, G, J and L,
  - y=1 only when:
    1) said ring members E, G, J, and L are all simultaneously carbon atoms and $R_7$ is attached to said nitrogen atom of the unsaturated ring; or alternatively
    2) at least one of the ring members E, G, J, and L is a nitrogen atom to which $R_7$ is attached;
- when Z is an unsaturated cationic group of formula (III):
  - if x=0, then said linker arm D is attached to said nitrogen atom other than E, G, J, L, and M,
  - if x=1, then said linker arm D is attached to one of said ring members chosen from E, G, J, L, and M,
  - y=1 only when at least one of said ring members E, G, J, L and M is a divalent atom and $R_7$ is attached to said nitrogen atom of me unsaturated ring other than E, G, J, L and M; and when Z is a cationic group of formula (IV):
if x=0, then the linker arm D is attached to the nitrogen atom bearing said groups $R_8$, $R_9$ and $R_{10}$;
if x=1, then two of said groups $R_8$, $R_9$ and $R_{10}$ form, together with the nitrogen atom to which they are attached, a saturated ring chosen from a 5- and 6-membered rings as defined above, and said linker arm D is attached to a carbon atom of said saturated ring;
wherein in said compound of formula (I), at least one of $R_1$, $R_2$, $R_3$, A1, and 2 comprises at least one Z group.

14. A composition for the oxidation dyeing of keratin fibres according to claim 13, wherein said keratin fibres are human keratin fibres.

15. A composition for the oxidation dyeing of keratin fibres according to claim 14, wherein said human keratin fibres are hair.

16. A composition for the oxidation dyeing of keratin fibres according to claim 13, wherein said at least one coupler is present in a concentration ranging from 0.0005 to 12% by weight relative to the total weight of said composition.

17. A composition for the oxidation dyeing of keratin fibres according to claim 16, wherein said concentration ranges from 0.005% to 6% by weight relative to the total weight of said composition.

18. A composition for the oxidation dyeing of keratin fibres according to claim 13, further comprising at least one oxidation base chosen from para-phenylenediamine bases, bis(phenyl)alkylenediamines bases, para-aminophenol bases, ortho-aminophenol bases and heterocyclic bases.

19. A composition for the oxidation dyeing of keratin fibres according to claim 18, wherein said para-phenylenediamines are chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N—(β-hydroxypropyl)-para-phenylenediamine, 2-hydroxymethyl-para-phenylenediamine, N,N-dimethyl-3-methyl-para-phenylenediamine, N-ethyl-N—(β-hydroxyethyl)-para-phenylenediamine, N—(β,γ-dihydroxypropyl)-para-phenylenediamine, N—(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N—(β-methoxyethyl)-para-phenylenediamine, and acid addition salts thereof.

20. A composition for the oxidation dyeing of keratin fibres according to claim 18, wherein said bis(phenyl)alkylenediamines are chosen from N,NN-bis(β-hydroxyethyl)-N,NN-bis(4N-aminophenyl)-1,3-diaminopropanol, N,NN-bis(β-hydroxyethyl)-N,NN-bis(4N-aminophenyl)ethylenediamine, N,NN-bis(4-aminophenyl)tetramethylenediamine, N,NN-bis(β-hydroxyethyl)-N,NN-bis(4-aminophenyl)tetramethylenediamine, N,NN-bis(4-methylaminophenyl)tetramethylenediamine, N,NN-bis(ethyl)-N,NN-bis(4N-amino-3N-methylphenyl)ethylenediamine, 1,8-bis(2,5-diaminophenoxy)-3,5-dioxaoctane, and acid addition salts thereof.

21. A composition for the oxidation dyeing of keratin fibres according to claim 18, wherein said para-aminophenols are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid addition salts thereof.

22. A composition for the oxidation dyeing of keratin fibres according to claim 18, wherein said ortho-aminophenols are chosen from 2-aminophenol, 2-amino-5-methylphenol, 2-amino-6-methylphenol, 5-acetamido-2-aminohenol, and acid addition salts thereof.

23. A composition for the oxidation dyeing of keratin fibres according to claim 18, wherein said heterocyclic bases are chosen from pyridine derivatives, pyrimidine derivatives and pyrazole derivatives.

24. A composition for the oxidation dyeing of keratin fibres according to claim 18, wherein said at least one oxidation base is present in a concentration ranging from 0.0005 to 12% by weight relative to the total weight of said composition.

25. A composition for the oxidation dyeing of keratin fibres according to claim 24, wherein said concentration ranges from 0.005% to 6% by weight relative to the total weight of said composition.

26. A composition for the oxidation dyeing of keratin fibres according to claim 13, further comprising at least one second coupler other than said at least one coupler.

27. A composition for the oxidation dyeing of keratin fibres according to claim 26, wherein said at least one second coupler is chosen from a meta-phenylenediamine, meta-aminophenol, meta-diphenol, a heterocyclic coupler, and acid addition salts thereof.

28. A composition for the oxidation dyeing of keratin fibres according to claim 26, wherein said at least one second coupler is chosen from 2-methyl-5-aminophenol, 5-N—(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one and acid addition salts thereof.

29. A composition for the oxidation dyeing of keratin fibres according to claim 26, wherein said at least one second coupler is present in a concentration ranging from 0.0001% to 10% by weight relative to the total weight of said composition.

30. A composition for the oxidation dyeing of keratin fibres according to claim 29, wherein said concentration ranges from 0.005% to 5% by weight relative to the total weight of said composition.

31. A composition for the oxidation dyeing of keratin fibres according to claim 13, further comprising at least one direct dye.

32. A composition for the oxidation dyeing of keratin fibres according to claim 13, wherein said medium is chosen from water and a mixture of water and at least one organic solvent chosen from $C_1$–$C_4$ lower alkanols, glycerol, glycols, glycol ethers, aromatic alcohols, and mixtures thereof.

33. A composition for the oxidation dyeing of keratin fibres according to claim 32, herein said at least one solvent is present in proportions ranging from about 1% to about 40% by weight relative to the total weight of said compositions.

34. A composition for the oxidation dyeing of keratin fibres according to claim 13, further comprising at least one adjuvant chosen from anionic surfactants, cationic surfactants, nonionic surfactants, amphoteric surfactants, zwitterionic surfactants, anionic polymers, cationic polymers, nonionic polymers, amphoteric polymers, zwitterionic polymers, inorganic thickeners, organic thickeners, antioxidants, penetration agents, sequestering agents, fragrances, buffers, dispersing agents, packaging agents, silicones, film-forming agents, ceramides, preserving agents and opacifiers.

35. A composition for the oxidation dyeing of keratin fibres according to claim 13, further comprising at least one agent chosen from acidifying agents and basifying agents.

36. A composition for the oxidation dyeing of keratin fibres according to claim 13, having a pH ranging from 3 to 12.

37. A composition for the oxidation dyeing of keratin fibres according to claim 13, wherein said composition is in a form chosen from liquids, creams and gels.

38. A composition according to claim 13, wherein said acid addition salts are chosen from a hydrochloride, a hydrobromide, a sulphate, a citrate, a succinate, a tartrate, a lactate and an acetate.

39. A process for oxidation dyeing of at least one keratin fibre, comprising applying to said keratin fibre at least one dye composition for a time sufficient to develop a coloration and also applying to said keratin fibre at least one oxidizing agent, said at least one oxidizing agent and said at least one dye composition being applied to said keratin fibres at the same time, either together or separately, or said at least one oxidizing agent and said at least one dye composition being applied sequentially to said keratin fibres, said at least one dye composition comprising, in a medium suitable for dyeing, at least one coupler chosen from compounds of formula (I) and acid addition salts thereof:

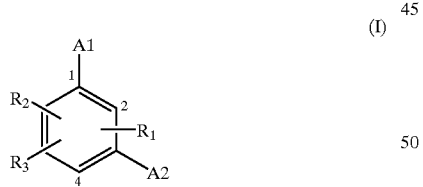

(I)

in which:

$R_1$, $R_2$ and $R_3$, which may be identical or different, are each chosen from hydrogen; halogens; Z groups; —CO—Z groups; —CO—OZ groups; ($C_1$–$C_6$) alkylcarbonyl groups; amino($C_1$–$C_6$)alkylcarbonyl groups; N—Z-amino($C_1$–$C_6$)alkylcarbonyl groups; N—($C_1$–$C_6$)alkylamino($C_1$–$C_6$)alkylcarbonyl groups; N,N-di($C_1$–$C_6$)alkylamino($C_1$–$C_6$)alkylcarbonyl groups; amino($C_1$–$C_6$)alkylcarbonyl($C_1$–$C_6$)alkyl groups; N—Z-amino($C_1$–$C_6$)alkylcarbonyl($C_1$–$C_6$) alkyl groups; N—($C_1$–$C_6$)alkylamino($C_1$–$C_6$-alkylcarbonyl($C_1$–$C_6$)alkyl groups; N,N-di($C_1$–$C_6$) alkylamino($C_1$–$C_6$)alkylcarbonyl-($C_1$–$C_6$)alkyl groups; a carboxyl group; ($C_1$–$C_6$)alkylcarboxyl groups; $C_1$–$C_6$ alkylsulphonyl groups; aminosulphonyl groups; N—Z-aminosulphonyl groups; $C_1$–$C_6$ N-alkyl-aminosulphonyl groups; N,N-di($C_1$–$C_6$) alkylaminosulphonyl groups; $C_1$–$C_6$ aminosulphonylalkyl groups; $C_1$–$C_6$ N—Z-aminosulphonylalkyl groups; N—($C_1$–$C_6$)alkylaminosulphonyl($C_1$–$C_6$)alkyl groups; N,N-di($C_1$–$C_6$)alkylaminosulphonyl($C_1$–$C_6$) alkyl groups; a carbamyl group; N—($C_1$–$C_6$) alkylcarbamyl groups; N,N-di($C_1$–$C_6$)alkylcarbamyl groups; carbamyl($C_1$–$C_6$)alkyl groups; N—($C_1$–$C_6$) alkylcarbamyl($C_1$–$C_6$)alkyl groups; N,N-di($C_1$–$C_6$) alkylcarbamyl($C_1$–$C_6$)alkyl groups; $C_1$–$C_6$ alkyl groups; $C_1$–$C_6$ monohydroxyalkyl groups; $C_2$–$C_6$ polyhydroxyalkyl groups; ($C_1$–$C_6$)alkoxy($C_1$–$C_6$)alkyl groups; $C_1$–$C_6$ trifluoroalkyl groups; a cyano group; groups —$OR_6$; groups —$SR_6$; and amino groups protected with at least one group chosen from ($C_1$–$C_6$) alkylcarbonyl groups, ($C_1$–$C_6$)alkylcarboxyl groups, trifluoro($C_1$–$C_6$)alkylcarbonyl groups, amino($C_1$–$C_6$) alkylcarbonyl groups, N—Z-amino($C_1$–$C_6$) alkylcarbonyl groups, N—($C_1$–$C_6$)alkylamino($C_1$–$C_6$) alkylcarbonyl groups, N,N-di($C_1$–$C_6$)alkylamino ($C_1$–$C_6$)alkylcarbonyl groups, ($C_1$–$C_6$)alkylcarboxyl groups, a carbamyl group, N—($C_1$–$C_6$)alkylcarbamyl groups, N,N-di($C_1$–$C_6$)alkylcarbamyl groups, $C_1$–$C_6$ alkylsulphonyl groups, aminosulphonyl groups, N—Z-aminosulphonyl groups, $C_1$–$C_6$ N-alkylaminosulphonyl groups, N,N-di($C_1$–$C_6$) alkylaminosulphonyl groups, a thiocarbamyl group, a formyl group, —CO—Z groups, and —CO—OZ groups;

$R_6$ is chosen from $C_1$–$C_6$ alkyl groups; $C_1$–$C_6$ monohydroxyalkyl groups; $C_2$–$C_6$ polyhydroxyalkyl groups; groups Z; ($C_1$–$C_6$)alkoxy($C_1$–$C_6$)alkyl groups; aryl groups; a benzyl group; carboxy($C_1$–$C_6$)alkyl groups; ($C_1$–$C_6$)alkylcarboxy-($C_1$–$C_6$)alkyl groups; cyano ($C_1$–$C_6$)alkyl groups; carbamyl($C_1$–$C_6$)alkyl groups; N—($C_1$–$C_6$)alkylcarbamyl($C_1$–$C_6$)alkyl groups; N,N-di($C_1$–$C_6$)alkylcarbamyl($C_1$–$C_6$)alkyl groups; $C_1$–$C_6$ trifluoroalkyl groups; $C_1$–$C_6$ aminosulphonylalkyl groups; $C_1$–$C_6$ N—Z-aminosulphonylalkyl groups; N—($C_1$–$C_6$)alkylaminosulphonyl($C_1$–$C_6$)alkyl groups; N,N-di($C_1$–$C_6$)alkylaminosulphonyl($C_1$–$C_6$)alkyl groups; ($C_1$–$C_6$)alkylsulphinyl($C_1$–$C_6$)alkyl groups; ($C_1$–$C_6$)alkylsulphonyl($C_1$–$C_6$)alkyl groups; ($C_1$–$C_6$) alkylcarbonyl($C_1$–$C_6$)alkyl groups; $C_1$–$C_6$ aminoalkyl groups; $C_1$–$C_6$ aminoalkyl groups wherein said amino is substituted with one or two groups chosen from $C_1$–$C_6$ alkyl groups, $C_1$–$C_6$ monohydroxyalkyl groups, $C_2$–$C_6$ polyhydroxyalkyl groups, ($C_1$–$C_6$) alkylcarbonyl groups, a formyl group, trifluoro-($C_1$–$C_6$)alkylcarbonyl groups, ($C_1$–$C_6$)alkylearboxyl groups, a carbamyl group, N—($C_1$–$C_6$)alkylcarbamyl groups, N,N-di-($C_1$–$C_6$)alkylcarbamyl groups, a thiocarbamyl group, $C_1$–$C_6$ alkylsulphonyl groups, Z groups, —CO—Z groups, and —CO—OZ groups;

A1 is chosen from —$NR_4R_5$ groups and a hydroxyl group;

A2 is chosen from —NR=$_4$R=$_5$ groups and a hydroxyl group;

$R_4$, $R_5$, R=$_4$ and R=$_5$, which may be identical or different, are each chosen from hydrogen; Z groups; $C_1$–$C_6$ alkyl groups; $C_1$–$C_6$ monohydroxyalkyl groups; $C_2$–$C_6$ polyhydroxyalkyl groups; ($C_1$–$C_6$)alkoxy ($C_1$–$C_6$)alkyl groups; aryl groups; a benzyl group; cyano($C_1$–$C_6$)alkyl groups; carbamyl($C_1$–$C_6$)alkyl groups; N—($C_1$–$C_6$)alkylcarbamyl($C_1$–$C_6$)alkyl groups; N,N-di($C_1$–$C_6$)alkylcarbamyl($C_1$–$C_6$)alkyl groups; thiocarbamyl($C_1$–$C_6$)alkyl groups; $C_1$–$C_6$ trifluoroalkyl groups; $C_1$–$C_6$ sulphoalkyl groups; ($C_1$–$C_6$) alkylcarboxy($C_1$–$C_6$)alkyl groups; ($C_1$–$C_6$) alkylsulphinyl($C_1$–$C_6$)alkyl groups; $C_1$–$C_6$ aminosulphonylalkyl groups; $C_1$–$C_6$ N—Z-aminosulphonylalkyl groups; N—($C_1$–$C_6$) alkylaminosulphonyl($C_1$–$C_6$)alkyl groups; N,N-di($C_1$–$C_6$)alkylaminosulphonyl($C_1$–$C_6$)alkyl groups; ($C_1$–$C_6$)alkylcarbonyl($C_1$–$C_6$)alkyl groups; $C_1$–$C_6$ aminoalkyl groups; $C_1$–$C_6$ aminoalkyl groups wherein said amino is substituted with one or two groups chosen from $C_1$–$C_6$ alkyl groups, $C_1$–$C_6$ monohydroxyalkyl groups, $C_2$–$C_6$ polyhydroxyalkyl groups, ($C_1$–$C_6$) alkylcarbonyl groups, a carbamyl group, N—($C_1$–$C_6$) alkylcarbamyl groups, N,N-di($C_1$–$C_6$)alkylcarbamyl groups, $C_1$–$C_6$ alkylsulphonyl groups, a formyl group, trifluoro($C_1$–$C_6$)alkylcarbonyl groups, ($C_1$–$C_6$) alkylcarboxyl groups, thiocarbamyl groups, Z groups, —CO—Z groups, and —CO—OZ groups;

one and only one of the groups $R_4$, R=$_4$, $R_5$ and R=$_5$ may also be chosen from($C_1$–$C_6$)alkylcarboxyl groups; ($C_1$–$C_6$)alkylcarbonyl groups; a formyl group; trifluoro($C_1$–$C_6$)alkylcarbonyl groups; amino($C_1$–$C_6$) alkylcarbonyl groups; N—Z-amino($C_1$–$C_6$) alkylcarbonyl groups; N—($C_1$–$C_6$)alkylamino($C_1$–$C_6$) alkylcarbonyl groups; N,N-di($C_1$–$C_6$)alkylamino($C_1$–$C_6$)alkylcarbonyl groups; a carbamyl group; N—($C_1$–$C_6$)alkylcarbamyl groups; N,N-di($C_1$–$C_6$) alkylcarbamyl groups; a thiocarbamyl group; an aminosulphonyl group; N—Z-aminosulphonyl groups; N—($C_1$–$C_6$)alkylaminosulphonyl groups; N,N-di($C_1$–$C_6$)alkylaminosulphonyl groups; ($C_1$–$C_6$) alkylsulphonyl groups; —CO—Z groups; and —CO—OZ groups;

Z, which may be identical or different, is chosen from unsaturated cationic groups of formula (II), unsaturated cationic groups of formula (III), and saturated cationic groups of formula (IV):

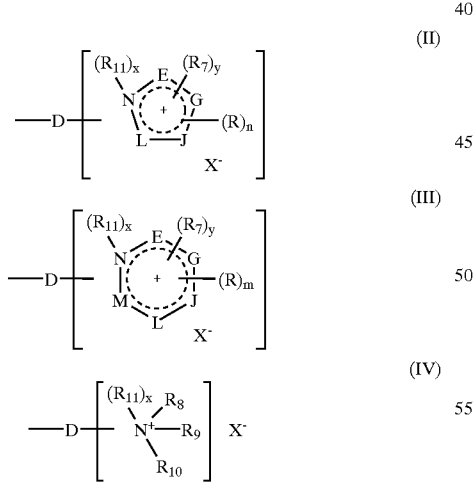

in which:

D is a linker arm chosen form linear and branched divalent alkyl chains, wherein said linear and branched divalent alkyl chains can be interrupted by at least one heteroatom, and further wherein said linear and branched divalent alkyl chains can be substituted with at least one group chosen from a hydroxyl group and $C_1$–$C_6$ alkoxy groups;

ring members E, G, J, L and M, which may be identical or different, are each chosen from carbon, oxygen, sulphur, and nitrogen;

n is an integer chosen from 0 to 4 inclusive;

m is an integer chosen from 0 to 5 inclusive;

the groups R, which may be identical or different, are each chosen from additional Z groups which may be identical to or different from other Z groups, halogens, hydroxyl groups, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri($C_1$–$C_6$)alkylsilane($C_1$–$C_6$)alkyl groups, an amido group, an aldehydo group, a carboxyl group, ($C_1$–$C_6$) alkylcarbonyl groups, a thio group, $C_1$–$C_6$ thioalkyl groups, $C_1$–$C_6$ alkylthio groups, an amino group, amino groups protected with at least one group chosen from ($C_1$–$C_6$)alkylcarbonyl groups, a carbamyl group, and $C_1$–$C_6$ alkylsulphonyl groups, and NHR=== groups and NR=== R==== groups wherein R=== and R====, which may be identical or different, are each chosen from $C_1$–$C_6$ alkyl groups, $C_1$–$C_6$ monohydroxyalkyl groups and $C_2$–$C_6$ polyhydroxyalkyl groups;

when n is greater than or equal to 2, two of the adjacent R groups may also form together an unsaturated ring chosen from 5- and 6-membered carbon-based rings and rings containing at least one hetero atom;

$R_7$ is chosen from $C_1$–$C_6$ alkyl groups, $C_1$–$C_6$ monohydroxyalkyl groups, $C_2$–$C_6$ polyhydroxyalkyl groups, cyano($C_1$–$C_6$)alkyl groups, tri($C_1$–$C_6$) alkylsilane($C_1$–$C_6$)alkyl groups, ($C_1$–$C_6$)alkoxy ($C_1$–$C_6$)alkyl groups, carbamyl-($C_1$–$C_6$)alkyl groups, ($C_1$–$C_6$)alkylcarboxy($C_1$–$C_6$)-alkyl groups, and a benzyl group;

$R_8$, $R_9$ and $R_{10}$, which may be identical or different, are each chosen from $C_1$–$C_6$ alkyl groups, $C_1$–$C_6$ monohydroxyalkyl groups, $C_2$–$C_6$ polyhydroxyalkyl groups, ($C_1$–$C_6$)alkoxy($C_1$–$C_6$)alkyl groups, cyano ($C_1$–$C_6$)alkyl groups, aryl groups, a benzyl group, $C_1$–$C_6$ amidoalkyl groups, tri($C_1$–$C_6$)alkylsilane ($C_1$–$C_6$)alkyl groups, and $C_1$–$C_6$ aminoalkyl groups wherein said amino is protected with at least one group chosen from ($C_1$–$C_6$)alkylcarbonyl groups, a carbamyl group and $C_1$–$C_6$ alkylsulphonyl groups; two of said groups $R_8$, $R_9$ and $R_{10}$ can together optionally form, with the nitrogen atom to which they are attached, a saturated ring chosen from 5- and 6-membered carbon-based rings containing at least one heteroatom, wherein said ring is optionally substituted with at least one group chosen from halogens, a hydroxyl group, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri($C_1$–$C_6$)alkylsilane($C_1$–$C_6$)alkyl groups, an amido group, an aldehydo group, a carboxyl group, keto ($C_1$–$C_6$)alkyl groups, a thio group, $C_1$–$C_6$ thioalkyl groups, $C_1$–$C_6$ alkylthio groups, an amino group, and amino groups protected with at least one group chosen from ($C_1$–$C_6$)alkylcarbonyl groups, a carbamyl group and $C_1$–$C_6$ alkylsulphonyl groups;

$R_{11}$ is chosen from $C_1$–$C_6$ alkyl groups, $C_1$–$C_6$ monohydroxyalkyl groups, $C_2$–$C_6$ polyhydroxyalkyl groups, aryl groups, a benzyl group, $C_1$–$C_6$ aminoalkyl groups, carboxy($C_1$–$C_6$)alkyl groups, cyano ($C_1$–$C_6$)alkyl groups, carbamyl($C_1$–$C_6$)alkyl groups, $C_1$–$C_6$ trifluoroalkyl groups, tri($C_1$–$C_6$)alkylsilane ($C_1$–$C_6$)alkyl groups, $C_1$–$C_6$ sulphonamidoalkyl groups, ($C_1$–$C_6$)alkylcarboxy($C_1$–$C_6$)alkyl groups, ($C_1$–$C_6$)alkylsulphinyl($C_1$–$C_6$)alkyl groups, ($C_1$–$C_6$) alkylsulphonyl($C_1$–$C_6$)alkyl groups, ($C_1$–$C_6$) alkylketo($C_1$–$C_6$)alkyl groups, N—($C_1$–$C_6$) alkylcarbamyl($C_1$–$C_6$)alkyl groups N—($C_1$–$C_6$) alkylsulphonamido($C_1$–$C_6$)alkyl groups, and $C_1$–$C_6$ aminoalkyl groups wherein said amino is protected with at least one group chosen from ($C_1$–$C_6$) alkylcarbonyl groups, a carbamyl group and $C_1$–$C_6$ alkylsulphonyl groups; and x and y, which may be identical or different, are integers chosen from 0 and 1;

X is chosen from a monovalent anion and a divalent anion; and provided that:
  when Z is an unsaturated cationic group of formula (II):
    if x=0, then said linker arm D is attached to said nitrogen atom other than E, G, J, and L,
    if x=1, then said linker arm D is attached to one of said ring members chosen from E, G, J and L,
    y=1 only when:
      1) said ring members E, G, J, and L are all simultaneously carbon atoms and $R_7$ is attached to said nitrogen atom of the unsaturated ring ; or alternatively
      2) at least one of the ring members E, G, J, and L is a nitrogen atom to which $R_7$ is attached;
  when Z is an unsaturated cationic group of formula (III):
    if x=0, then said linker arm D is attached to said nitrogen atom other than E, G, J, L, and M,
    if x=1, then said linker arm D is attached to one of said ring members chosen from E, G, J, L, and M,
    y=1 only when at least one of said ring members E, G, J, L and M is a divalent atom and $R_7$ is attached to said nitrogen atom of the unsaturated ring other than E, G, J, L and M; and
  when Z is a cationic group of formula (IV):
    if x=0, then the linker arm D is attached to the nitrogen atom bearing said groups $R_8$, $R_9$ and $R_{10}$;
    if x=1, then two of said groups $R_8$, $R_9$ and $R_{10}$ form, together with the nitrogen atom to which they are attached, a saturated ring chosen from a 5- and 6-membered rings as defined above, and said linker arm D is attached to a carbon atom of said saturated ring;
wherein in said compound of formula (I), at least one of $R_1$, $R_2$, $R_3$ A1, and A2 comprises at least one Z group.

40. A process according to claim 39, wherein said keratin fibre is hair.

41. A process according to claim 39, wherein said at least one oxidizing agent is chosen from hydrogen peroxide, urea peroxide, alkali metal bromates, persalts, and enzymes.

42. A process according to claim 41, wherein said persalts are chosen from perborates and persulphates.

43. A process according to claim 41, wherein said enzymes are chosen from peroxidases and 2-electron oxidoreductases.

44. A multi-compartment dyeing kit, comprising a first compartment containing at least one dye composition, and a second compartment containing at least one oxidizing agent, wherein said at least one dye composition comprises, in a medium suitable for dyeing, at least one coupler chosen from compounds of formula (I) and acid addition salts thereof:

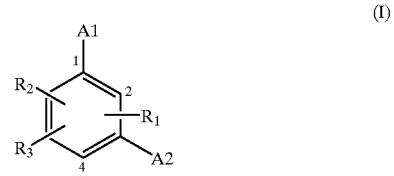

in which:
  $R_1$, $R_2$ and $R_3$, which may be identical or different, are each chosen from hydrogen; halogens; Z groups; —CO—Z groups; —CO—OZ groups; ($C_1$–$C_6$) alkylcarbonyl groups; amino($C_1$–$C_6$)alkylcarbonyl groups; N—Z-amino($C_1$–$C_6$)alkylcarbonyl groups; N—($C_1$–$C_6$)alkylamino($C_1$–$C_6$)alkylcarbonyl groups; N,N-di($C_1$–$C_6$)alkylamino($C_1$–$C_6$)alkylcarbonyl groups; amino($C_1$–$C_6$)alkylcarbonyl($C_1$–$C_6$)alkyl groups; N—Z-amino($C_1$–$C_6$)alkylcarbonyl($C_1$–$C_6$) alkyl groups; N—($C_1$–$C_6$)alkylamino($C_1$–$C_6$) alkylcarbonyl($C_1$–$C_6$)alkyl groups; N,N-di($C_1$–$C_6$) alkylamino($C_1$–$C_6$)alkylcarbonyl-($C_1$–$C_6$)alkyl groups; a carboxyl group; ($C_1$–$C_6$)alkylcarboxyl groups; $C_1$–$C_6$ alkylsulphonyl groups; aminosulphonyl groups; N—Z-aminosulphonyl groups; $C_1$–$C_6$ N-alkylaminosulphonyl groups; N,N-di($C_1$–$C_6$) alkylaminosulphonyl groups; $C_1$–$C_6$ aminosulphonylalkyl groups; $C_1$–$C_6$ N—Z-aminosulphonylalkyl groups; N—($C_1$–$C_6$)alkylaminosulphonyl($C_1$–$C_6$)alkyl groups; N,N-di($C_1$–$C_6$)alkylaminosulphonyl($C_1$–$C_6$) alkyl groups; a carbamyl group; N—($C_1$–$C_6$) alkylcarbamyl groups; N,N-di($C_1$–$C_6$)alkylcarbamyl groups; carbamyl($C_1$–$C_6$)alkyl groups; N—($C_1$–$C_6$) alkylcarbamyl($C_1$–$C_6$)alkyl groups; N,N-di($C_1$–$C_6$) alkylcarbamyl($C_1$–$C_6$)alkyl groups; $C_1$–$C_6$ alkyl groups; $C_1$–$C_6$ monohydroxyalkyl groups; $C_2$–$C_6$ polyhydroxyalkyl groups; ($C_1$–$C_6$)alkoxy($C_1$–$C_6$)alkyl groups; $C_1$–$C_6$ trifluoroalkyl groups; a cyano group; groups —$OR_6$; groups —$SR_6$; and amino groups protected with at least one group chosen from ($C_1$–$C_6$) alkylcarbonyl groups, ($C_1$–$C_6$)alkylcarboxyl groups, trifluoro($C_1$–$C_6$)alkylcarbonyl groups, amino($C_1$–$C_6$) alkylcarbonyl groups, N—Z-amino($C_1$–$C_6$) alkylcarbonyl groups, N—($C_1$–$C_6$)alkylamino($C_1$–$C_6$) alkylcarbonyl groups, N,N-di($C_1$–$C_6$)alkylamino ($C_1$–$C_6$)alkylcarbonyl groups, ($C_1$–$C_6$)alkylcarboxyl groups, a carbamyl group, N—($C_1$–$C_6$)alkylcarbamyl groups, N,N-di($C_1$–$C_6$)alkylcarbamyl groups, $C_1$–$C_6$ alkylsulphonyl groups, aminosulphonyl groups, N—Z-aminosulphonyl groups, $C_1$–$C_6$ N-alkylaminosulphonyl groups, N,N-di($C_1$–$C_6$) alkylaminosulphonyl groups, a thiocarbamyl group, a formyl group, —CO—Z groups, and —CO—OZ groups;

$R_6$ is chosen from $C_1$–$C_6$ alkyl groups; $C_1$–$C_6$ monohydroxyalkyl groups; $C_2$–$C_6$ polyhydroxyalkyl groups; groups Z; ($C_1$–$C_6$)alkoxy($C_1$–$C_6$)alkyl groups; aryl groups; a benzyl group; carboxy($C_1$–$C_6$)alkyl groups; ($C_1$–$C_6$)alkylcarboxy-($C_1$–$C_6$)alkyl groups; cyano ($C_1$–$C_6$)alkyl groups; carbamyl($C_1$–$C_6$)alkyl groups; N—($C_1$–$C_6$)alkylcarbamyl($C_1$–$C_6$)alkyl groups; N,N-di($C_1$–$C_6$)alkylcarbamyl($C_1$–$C_6$)alkyl groups; $C_1$–$C_6$ trifluoroalkyl groups; $C_1$–$C_6$ aminosulphonylalkyl groups; $C_1$–$C_6$ N—Z-aminosulphonylalkyl groups; N—($C_1$–$C_6$)alkylaminosulphonyl($C_1$–$C_6$)alkyl groups; N,N-di($C_1$–$C_6$)alkylaminosulphonyl($C_1$–$C_6$)alkyl groups; $(C_1-C_6)$alkylsulphinyl$(C_1-C_6)$alkyl groups; $(C_1-C_6)$alkylsulphonyl$(C_1-C_6)$alkyl groups; $(C_1-C_6)$alkylcarbonyl$(C_1-C_6)$alkyl groups; $C_1-C_6$ aminoalkyl groups; $C_1-C_6$ aminoalkyl groups wherein said amino is substituted with one or two groups chosen from $C_1-C_6$ alkyl groups, $C_1-C_6$ monohydroxyalkyl groups, $C_2-C_6$ polyhydroxyalkyl groups, $(C_1-C_6)$alkylcarbonyl groups, a formyl group, trifluoro-$(C_1-C_6)$alkylcarbonyl groups, $(C_1-C_6)$alkylcarboxyl groups, a carbamyl group, N—$(C_1-C_6)$alkylcarbamyl groups, N,N-di-$(C_1-C_6)$alkylcarbamyl groups, a thiocarbamyl group, $C1-C_6$ alkylsulphonyl groups, Z groups, —CO—Z groups, and —CO—OZ groups;

A1 is chosen from —$NR_4R_5$ groups and a hydroxyl group;

A2 is chosen from —$NR={_4}R={_5}$ groups and a hydroxyl group;

$R_4$, $R_5$, $R={_4}$ and $R={_5}$, which may be identical or different, are each chosen from hydrogen; Z groups; $C_1-C_6$ alkyl groups; $C_1-C_6$ monohydroxyalkyl groups; $C_2-C_6$ polyhydroxyalkyl groups; $(C_1-C_6)$alkoxy$(C_1-C_6)$alkyl groups; aryl groups; a benzyl group; cyano$(C_1-C_6)$alkyl groups; carbamyl$(C_1-C_6)$alkyl groups; N—$(C_1-C_6)$alkylcarbamyl$(C_1-C_6)$alkyl groups; N,N-di$(C_1-C_6)$alkylcarbamyl$(C_1-C_6)$alkyl groups; thiocarbamyl$(C_1-C_6)$alkyl groups; $C_1-C_6$ trifluoroalkyl groups; $C_1-C_6$ sulphoalkyl groups; $(C_1-C_6)$alkylcarboxy$(C_1-C_6)$alkyl groups; $(C_1-C_6)$alkylsulphinyl$(C_1-C_6)$alkyl groups; $C_1-C_6$ aminosulphonylalkyl groups; $C_1-C_6$ N—Z-aminosulphonylalkyl groups; N—$(C_1-C_6)$alkylaminosulphonyl$(C_1-C_6)$alkyl groups; N,N-di$(C_1-C_6)$alkylaminosulphonyl$(C_1-C_6)$alkyl groups; $(C_1-C_6)$alkylcarbonyl$(C_1-C_6)$alkyl groups; $C_1-C_6$ aminoalkyl groups; $C_1-C_6$ aminoalkyl groups wherein said amino is substituted with one or two groups chosen from $C_1-C_6$ alkyl groups, $C_1-C_6$ monohydroxyalkyl groups, $C_2-C_6$ polyhydroxyalkyl groups, $(C_1-C_6)$alkylcarbonyl groups, a carbamyl group, N—$(C_1-C_6)$alkylcarbamyl groups, N,N-di$(C_1-C_6)$alkylcarbamyl groups, $C_1-C_6$ alkylsulphonyl groups, a formyl group, trifluoro$(C_1-C_6)$alkylcarbonyl groups, $(C_1-C_6)$alkylcarboxyl groups, thiocarbamyl groups, Z groups, —CO—Z groups, and —CO—OZ groups;

one and only one of the groups $R_4$, $R={_4}$, $R_5$ and $R={_5}$ may also be chosen from $(C_1-C_6)$alkylcarboxyl groups; $(C_1-C_6)$alkylcarbonyl groups; a formyl group; trifluoro$(C_1-C_6)$alkylcarbonyl groups; amino$(C_1-C_6)$alkylcarbonyl groups; N—Z-amino$(C_1-C_6)$alkylcarbonyl groups; N—$(C_1-C_6)$alkylamino$(C_1-C_6)$alkylcarbonyl groups; N,N-di$(C_1-C_6)$alkylamino$(C_1-C_6)$alkylcarbonyl groups; a carbamyl group; N—$(C_1-C_6)$alkylcarbamyl groups; N,N-di$(C_1-C_6)$alkylcarbamyl groups; a thiocarbamyl group; an aminosulphonyl group; N—Z-aminosulphonyl groups; N—$(C_1-C_6)$alkylaminosulphonyl groups; N,N-di$(C_1-C_6)$alkylaminosulphonyl groups; $(C_1-C_6)$alkylsulphonyl groups; —CO—Z groups; and —CO—OZ groups;

Z, which may be identical or different, is chosen from unsaturated cationic groups of formula (II), unsaturated cationic groups of formula (III), and saturated cationic groups of formula (IV):

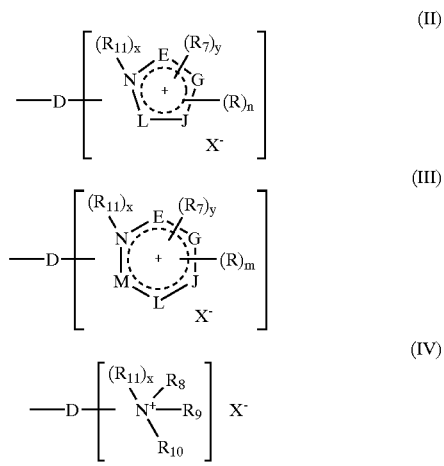

in which:

D is a linker arm chosen form linear and branched divalent alkyl chains, wherein said linear and branched divalent alkyl chains can be interrupted by at least one heteroatom, and further wherein said linear and branched divalent alkyl chains can be substituted with at least one group chosen from a hydroxyl group and $C_1-C_6$ alkoxy groups;

ring members E, G, J, L and M, which may be identical or different, are each chosen from carbon, oxygen, sulphur, and nitrogen;

n is an integer chosen from 0 to 4 inclusive;

m is an integer chosen from 0 to 5 inclusive;

the groups R, which may be identical or different, are each chosen from additional Z groups which may be identical to or different from other Z groups, halogens, hydroxyl groups, $C_1-C_6$ alkyl groups, $C_1-C_6$ monohydroxyalkyl groups, $C_2-C_6$ polyhydroxyalkyl groups, a nitro group, a cyano group, cyano$(C_1-C_6)$alkyl groups, $C_1-C_6$ alkoxy groups, tri$(C_1-C_6)$alkylsilane$(C_1-C_6)$alkyl groups, an amido group, an aldehydo group, a carboxyl group, $(C_1-C_6)$alkylcarbonyl groups, a thio group, $C_1-C_6$ thioalkyl groups, $C_1-C_6$ alkylthio groups, an amino group, amino groups protected with at least one group chosen from $(C_1-C_6)$alkylcarbonyl groups, a carbamyl group, and $C_1-C_6$ alkylsulphonyl groups, and NHR=== groups and NR=== R==== groups wherein R=== and R====, which may be identical or different, are each chosen from $C_1-C_6$ alkyl groups, $C_1-C_6$ monohydroxyalkyl groups and $C_2-C_6$ polyhydroxyalkyl groups;

when n is greater than or equal to 2, two of the adjacent R groups may also form together an unsaturated ring chosen from 5- and 6-membered carbon-based rings and rings containing at least one hetero atom;

$R_7$ is chosen from $C_1-C_6$ alkyl groups, $C_1-C_6$ monohydroxyalkyl groups, $C_2-C_6$ polyhydroxyalkyl groups, cyano$(C_1-C_6)$alkyl groups, tri$(C_1-C_6)$alkylsilane$(C_1-C_6)$alkyl groups, $(C_1-C_6)$alkoxy$(C_1-C_6)$alkyl groups, carbamyl-$(C_1-C_6)$alkyl groups, $(C_1-C_6)$alkylcarboxy$(C_1-C_6)$-alkyl groups, and a benzyl group;

$R_8$, $R_9$ and $R_{10}$, which may be identical or different, are each chosen from $C_1-C_6$ alkyl groups, $C_1-C_6$ monohydroxyalkyl groups, $C_2-C_6$ polyhydroxyalkyl groups, $(C_1-C_6)$alkoxy$(C_1-C_6)$alkyl groups, cyano ($C_1$–$C_6$)alkyl groups, aryl groups, a benzyl group, $C_1$–$C_6$ amidoalkyl groups, tri($C_1$–$C_6$)alkylsilane ($C_1$–$C_6$)alkyl groups, and $C_1$–$C_6$ aminoalkyl groups wherein said amino is protected with at least one group chosen from ($C_1$–$C_6$)alkylcarbonyl groups, a carbamyl group and $C_1$–$C_6$ alkylsulphonyl groups; two of said groups $R_8$, $R_9$ and $R_{10}$ can together optionally form, with the nitrogen atom to which they are attached, a saturated ring chosen from 5- and 6-membered carbon-based rings containing at least one heteroatom, wherein said ring is optionally substituted with at least one group chosen from halogens, a hydroxyl group, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri($C_1$–$C_6$)alkylsilane($C_1$–$C_6$)alkyl groups, an amido group, an aldehydo group, a carboxyl group, keto ($C_1$–$C_6$)alkyl groups, a thio group, $C_1$–$C_6$ thioalkyl groups, $C_1$–$C_6$ alkylthio groups, an amino group, and amino groups protected with at least one group chosen from ($C_1$–$C_6$)alkylcarbonyl groups, a carbamyl group and $C_1$–$C_6$ alkylsulphonyl groups;

$R_{11}$ is chosen from $C_1$–$C_6$ alkyl groups, $C_1$–$C_6$ monohydroxyalkyl groups, $C_2$-$C_6$ polyhydroxyalkyl groups, aryl groups, a benzyl group, $C_1$–$C_6$ aminoalkyl groups, carboxy($C_1$–$C_6$)alkyl groups, cyano($C_1$–$C_6$)alkyl groups, carbamyl($C_1$–$C_6$)alkyl groups, $C_1$–$C_6$ trifluoroalkyl groups, tri($C_1$–$C_6$)alkylsilane ($C_1$–$C_6$)alkyl groups, $C_1$–$C_6$ sulphonamidoalkyl groups, ($C_1$–$C_6$)alkylcarboxy($C_1$–$C_6$)alkyl groups, ($C_1$–$C_6$)alkylsulphinyl($C_1$–$C_6$)alkyl groups, ($C_1$–$C_6$) alkylsulphonyl($C_1$–$C_6$)alkyl groups, N—($C_1$–$C_6$) alkylsulphonamido($C_1$–$C_6$)alkyl groups, and $C_1$–$C_6$ aminoalkyl groups wherein said amino is protected with at least one group chosen from ($C_1$–$C_6$) alkylcarbonyl groups, a carbamyl group and $C_1$–$C_6$ alkylsulphonyl groups; and x and y, which may be identical or different, are integers chosen from 0 and 1;

$X^-$ is chosen from a monovalent anion and a divalent anion; and provided that:

when Z is an unsaturated cationic group of formula (II):
if x=0, then said linker arm D is attached to said nitrogen atom other than E, G, J and L,
if x=1, then said linker arm D is attached to one of said ring members chosen from E, G, J and L,
y=1 only when:
1) said ring members E, G, J, and L are all simultaneously carbon atoms and $R_7$ is attached to said nitrogen atom of the unsaturated ring; or alternatively
2) at least one of the ring members E, G, J, and L is a nitrogen atom to which $R_7$ is attached;

when Z is an unsaturated cationic group of formula (III);
if x=0, then said linker arm D is attached to said nitrogen atom other than E, G, J, L, and M,
if x=1, then said linker arm D is attached to one of said ring members chosen from E, G, J, L, and M,
y=1 only when at least one of said ring members E, G, J, L and M is a divalent atom and $R_7$ is attached to said nitrogen atom of the unsaturated ring other than E, G, J, L and M; and when Z is a cationic group of formula (IV):
if x=0, then the linker arm D is attached to the nitrogen atom bearing said groups $R_8$, $R_9$ and $R_{10}$;
if x1, then two of said groups $R_8$, $R_9$ and $R_{10}$ form, together with the nitrogen atom to which they are attached, a saturated ring chosen from a 5- and 6-membered rings as defined above, and said linker arm D is attached to a carbon atom of said saturated ring;

wherein in said formula (I) at least one of $R_1$, $R_2$, $R_3$, A1, and A2 comprises at least one Z group.

* * * * *

UNITED STATES PATENT AND TRADEMARK OFFICE
CERTIFICATE OF CORRECTION

PATENT NO. : 6,461,389 B1
DATED : October 8, 2002
INVENTOR(S) : Alain Genet et al.

It is certified that error appears in the above-identified patent and that said Letters Patent is hereby corrected as shown below:

Title Page,
Item (57), ABSTRACT,
Line 5, after "fibres", insert a comma.

Column 15,
Line 54, "With at least" should read -- with at least --.

Column 16,
Line 3, "Z;($C_1$-$C_6$)alkoxy($C_1$-$C_6$)alkyl" should read -- Z; ($C_1$-$C_6$)alkoxy($C_1$-$C_6$)alkyl --; and "groups: aryl" should read -- groups; aryl--.
Line 13, "groups;($C_1$-$C_6$)alkylsulphinyl($C_1$-$C_6$)alkyl" should read -- groups; ($C_1$-$C_6$)alkylsulphinyl($C_1$-$C_6$)alkyl --.
Lines 33-34, "groups;($C_1$-$C_6$)alkoxy($C_1$-$C_6$)alkyl" should read -- groups; ($C_1$-$C_6$)alkoxy($C_1$-$C_6$)alkyl --.
Lines 40-41, "groups;($C_1$-$C_6$)alkylsulphinyl($C_1$-$C_6$)alkyl" should read -- groups; ($C_1$-$C_6$)alkylsulphinyl($C_1$-$C_6$)alkyl --.
Line 58, "from($C_1$-$C_6$)alkylcarboxyl" should read -- from ($C_1$-$C_6$)alkylcarboxyl --.

Column 17,
Line 7, "formula (III," should read -- formula (III), --.
Line 30, "chosen form" should read -- chosen from --.
Lines 56-57, "NHR= groups and NR= R= groups wherein R= and R=,"
should read -- NHR== groups and NR==R=== groups wherein R= = and R===, --.
Line 65, "$C_1$-$C_6$, alkyl" should read -- $C_1$-$C_6$ alkyl --.

Column 18,
Lines 37-38, "tri($C_1$-$C_6$alkylsilane($C_1$-$C_6$)alkyl" should read -- tri($C_1$-$C_6$)alkylsilane($C_1$-$C_6$)alkyl --.
Line 39, "($C_1$-$C_6$)alkylcarboxyl($C_1$-$C_6$)alkyl" should read -- ($C_1$-$C_6$)alkylcarboxy($C_1$-$C_6$)alkyl --.
Line 51, "x is chosen" should read -- $X^-$ is chosen --.
Line 56, after "other", delete the comma.

Column 19,
Line 40, "an thiazole" should read -- a thiazole --.
Lines 42-43, "bezoxazolinium" should read -- benzoxazolinium --.
Line 58, "X is chosen" should read -- $X^-$ is chosen --.

UNITED STATES PATENT AND TRADEMARK OFFICE
CERTIFICATE OF CORRECTION

PATENT NO. : 6,461,389 B1
DATED : October 8, 2002
INVENTOR(S) : Alain Genet et al.

It is certified that error appears in the above-identified patent and that said Letters Patent is hereby corrected as shown below:

Column 20,
Lines 25-26, "N,N-bis[2-(3-methyl-3H-imidazol-1 -ium)ethyl]benzene-l,3-diamine" should read -- N,N-bis[2-(3-methyl-3H-imidazol-1-ium)ethyl]benzene-1,3-diamine --.

Column 21,
Line 51, "$C_2$-$C_6$polyhydroxyalkyl" should read -- $C_2$-$C_6$ polyhydroxyalkyl --.

Column 22,
Line 61, "chosen form" should read -- chosen from --.

Column 23,
Line 15, "$C_1$-$C_6$, thioalkyl" should read -- $C_1$-$C_6$ thioalkyl --.
Line 18, "($C_1$-$C_6$)alkylcarbonyI" should read -- ($C_1$-$C_6$)alkylcarbonyl --.
Lines 20-21, "NHR= groups and NR= R= groups wherein R= and R=," should read -- NHR== groups and NR==R=== groups wherein R== and R===, --.
Lines 31-32, "tri($C_1$-$C_6$)alkylsilane($C_1$ -$C_6$)alkyl" should read -- tri($C_1$-$C_6$)alkylsilane($C_1$-$C_6$)alkyl --.

Column 24,
Line 14, "be Identical" should read -- be identical --.
Line 16, "x⁻ is chosen" should read -- X⁻ is chosen --.
Line 44, "M ;" should read -- M; --.

Column 25,
Lines 61-62, "N,N-di($C_{C6}$)alkylcarbamyl($C_1$-$C_6$)alkyl" should read -- N,N-di($C_1$-$C_6$)alkylcarbamyl($C_1$-$C_6$)alkyl --.

Column 26,
Line 49, "from($C_1$-$C_6$)alkylcarboxyl" should read -- from ($C_1$-$C_6$)alkylcarboxyl --.

Column 27,
Line 22, "chosen form" should read -- chosen from --.
Line 47, "NR== R===" should read -- NR==R=== --.
Lines 50-51, "$C_1$-$C_6$ polyhydroxyalkyl" should read -- $C_2$-$C_6$ polyhydroxyalkyl --.
Line 57, "$C_1$-$C_6$ polyhydroxyalkyl" should read -- $C_2$-$C_6$ polyhydroxyalkyl --.

Column 28,
Line 66, "me unsaturated" should read -- the unsaturated --.

UNITED STATES PATENT AND TRADEMARK OFFICE
CERTIFICATE OF CORRECTION

PATENT NO. : 6,461,389 B1
DATED : October 8, 2002
INVENTOR(S) : Alain Genet et al.

It is certified that error appears in the above-identified patent and that said Letters Patent is hereby corrected as shown below:

Column 29,
Line 11, "2 comprises" should read -- A2 comprises --.
Line 31, "bis(phenyl)alkylenediamines" should read -- bis(phenyl)alkylenediamine --.
Line 60, "N,NN-bis(β-" should read -- N,N-bis(β- --;
Line 61, "hydroxyethyl)-N,NN-bis(4N-aminophenyl)-1,3-" should read
-- hydroxyethyl)-N,N-bis(4N-aminophenyl)-1,3- --;
Line 62, "diaminopropanol, N,NN-bis(β-hydroxyethyl)-N,NN-bis" should read
-- diaminopropanol, N,N-bis(β-hydroxyethyl)-N,N-bis --;
Line 63, "(4N-aminophenyl)ethylenediamine, N,NN-bis(4" should read
-- (4N-aminophenyl)ethylenediamine, N,N-bis(4 --
Line 64, "aminophenyl)tetramethylenediamine, N,NN-bis(β-" should read
-- aminophenyl)tetramethylenediamine, N,N-bis(β- --;
Line 65, "hydroxyethyl)-N,NN-bis(4-aminophenyl)" should read
-- hydroxyethyl)-N,N-bis(4-aminophenyl) --;
Line 66, "tetramethylenediamine, N,NN-bis(4-methylaminophenyl)" should read
-- tetramethylenediamine, N,N-bis(4-methylaminophenyl) --;
Line 67, "tetramethylenediamine, N,NN-bis(ethyl)-N,NN-bis(4N-" should read
-- tetramethylenediamine, N,N-bis(ethyl)-N,N-bis(4N- --.

Column 31,
Line 5, "herein" should read -- wherein --.
Line 31, "a succinate ,a tartrate," should read -- a succinate, a tartrate, --.
Lines 64-65, "N-($C_1$-$C_6$)alkylamino($C_1$-$C_6$-alkylcarbonyl($C_1$-$C_6$)alkyl" should read
-- N-($C_1$-$C_6$)alkylamino($C_1$-$C_6$)-alkylcarbonyl($C_1$-$C_6$)alkyl --.

Column 32,
Line 52, "($C_1$-$C_6$)alkylearboxyl" should read -- ($C_1$-$C_6$)alkylcarboxyl --.

Column 33,
Line 22, "from($C_1$-$C_6$)alkylcarboxyl" should read -- from ($C_1$-$C_6$)alkylcarboxyl --.
Line 61, "chosen form" should read -- chosen from --.

Column 34,
Line 20, "NR== R=== groups" should read -- NR==R=== groups --.

Column 35,
Line 7, after "groups", insert a comma.
Line 28, "ring ;" should read -- ring; --.

UNITED STATES PATENT AND TRADEMARK OFFICE
CERTIFICATE OF CORRECTION

PATENT NO. : 6,461,389 B1
DATED : October 8, 2002
INVENTOR(S) : Alain Genet et al.

It is certified that error appears in the above-identified patent and that said Letters Patent is hereby corrected as shown below:

Column 37,
Line 12, "C1-$C_6$ alkylsulphonyl" should read -- $C_1$-$C_6$ alkylsulphonyl --.
Line 49, "from($C_1$-$C_6$)alkylcarboxyl" should read -- from ($C_1$-$C_6$)alkylcarboxyl --.

Column 38,
Line 22, "chosen form" should read -- chosen from --.
Line 48, "NR== R=== groups" should read -- NR==R=== groups --.
Lines 59-60, "tri($C_1$-$C_6$)alkylsilane($C_1$ -$C_6$)alkyl" should read -- tri($C_1$-$C_6$)alkylsilane ($C_1$-$C_6$)alkyl --.

Column 39,
Lines 32-33, after "($C_1$-$C_6$)alkylsulphonyl($C_1$-$C_6$)alkyl groups,", insert
-- ($C_1$-$C_6$)alkylketo($C_1$-$C_6$)alkyl groups, N-($C_1$-$C_6$)alkylcarbamyl($C_1$-$C_6$)alkyl groups, --.

Column 40,
Line 18, "(III);" should read -- (III): --.
Line 30, "if x 1," should read -- if x = 1, --.

Signed and Sealed this

Seventeenth Day of June, 2003

JAMES E. ROGAN
*Director of the United States Patent and Trademark Office*